United States Patent
Leary et al.

(10) Patent No.: US 6,531,454 B1
(45) Date of Patent: Mar. 11, 2003

(54) GLYCOSYLATED POLYAMINES AND METHODS OF USE THEREFOR

(75) Inventors: Julie A. Leary, El Cerrito, CA (US); Sara P. Gaucher, Richmond, CA (US); Steven F. Pedersen, El Cerrito, CA (US)

(73) Assignee: The Regents of the University of California, Oakland, CA (US)

( * ) Notice: Subject to any disclaimer, the term of this patent is extended or adjusted under 35 U.S.C. 154(b) by 231 days.

(21) Appl. No.: 09/657,952

(22) Filed: Sep. 8, 2000

Related U.S. Application Data

(63) Continuation-in-part of application No. 09/524,729, filed on Mar. 14, 2000, now Pat. No. 6,420,344.
(60) Provisional application No. 60/124,559, filed on Mar. 16, 1999.

(51) Int. Cl.[7] .......................................... A61K 31/7028
(52) U.S. Cl. ...................... 514/42; 514/53; 536/17.2; 536/17.9; 536/29.1
(58) Field of Search .............................. 536/17.2, 17.9, 536/29.1; 514/42, 53

(56) References Cited

U.S. PATENT DOCUMENTS

| | | | |
|---|---|---|---|
| 3,710,795 A | 1/1973 | Higuchi et al. | 128/127 |
| 5,028,594 A | 7/1991 | Carson | 514/23 |
| 5,330,743 A | 7/1994 | Gibby et al. | 424/9 |
| 5,661,155 A | 8/1997 | Pendergast et al. | 514/267 |
| 5,789,418 A | 8/1998 | Keilhauer et al. | 514/296 |
| 5,874,413 A | 2/1999 | Townsend et al. | 514/43 |

FOREIGN PATENT DOCUMENTS

| | | |
|---|---|---|
| EP | 0 839 826 | 5/1998 |
| JP | 2001-166464 | 6/2001 |

OTHER PUBLICATIONS

Agnusdei D. and Iori, N. (2000). "Selective Estrogen Receptor Modulators (SERMs): Effects on Multiple Organ Systems," *Curr. Med. Chem.* 7(5):577–584.

Badger, A.M. et al. (1999). "Idoxifene, a Novel Selective Estrogen Receptor Modulator, is Effective in a Rat Model of Adjuvant–Induced Arthritis," *J. Pharmacol. Exp. Ther.* 291(3):1380–1386.

Cano, A. and Hermenegildo, C. (2000). "The Endometrial Effects of SERMs," *Hum. Reprod. Update* 6(3):244–254.

Chemical Abstract, Document No. 135:68569: Entry for JP Patent No. 2001–166464 located in STN file CAPlus: Accession No. 2001:451187 (4 pages total).

Dhingra, K. (1999). "Antiestrogens–Tamoxifen, SERMs and Beyond," *Invest. New Drugs* 17:285–311.

Evans, A. et al. (Aug. 1999). "Modern Antioestrogens and the Coming Revolution in Women's Health Care," *Aust. NZ. J. Obstet. Gynaecol.* 39(3):334–340.

Goldstein, S.R. et al. (2000). "A Pharmacological Review of Selective Oestrogen Receptor Modulators," *Hum. Reprod. Update* 6(3):212–224.

Grey, A.B. et al. (1995). "The Effect of the Anti–Estrogen Tamoxifen on Cardiovascular Risk Factors in Normal Postmenopausal Women," *J. Clin. Endocrinol. Metab.* 80(11):3191–3195.

Grey, A.B. et al. (1997). "The Anti–oestrogen Tamoxifen Produces Haemodilution in Normal Postmenopausal Women," *J. Intern. Med.* 242:383–388.

Guzzo, J.A. (Jan. 2000). "Selective Estrogen Receptor Modulators—A New Age of Estrogens in Cardiovascular Disease?" *Clin. Cardiol.* 23:15–17.

(List continued on next page.)

*Primary Examiner*—Kathleen K. Fonda
*Assistant Examiner*—Leigh C. Maier
(74) *Attorney, Agent, or Firm*—Morrison & Foerster LLP

(57) ABSTRACT

Glycosylated polyamines comprising of mono- or oligosaccharides that are glycosidically linked to an aliphatic polyamine, and pharmaceutically acceptable salts, prodrugs and derivatives thereof are provided. An exemplary glycosylated polyamine has the following structure:

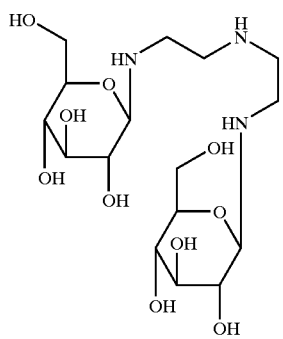

Glycosylated polyamines, their pharmaceutically acceptable salts, prodrugs and derivatives are useful, for example, as anticancer compounds for the treatment of a variety of cancers. Methods for synthesis of glycosylated polyamines are disclosed. In addition, metal complexes of glycosylated polyamines, the preparation of such metal complexes, analytical methods using the metal complexes are provided. Methods for detecting equatorial and axial conformation of a group other than hydrogen at the C2 position of a saccharide molecule are also provided. The compounds of the invention can be used as anti-cancer agents (e.g., against breast, ovarian, colon or renal cancers). Furthermore, the compounds of the invention are ligands for the estrogen receptor and thus can be used to modulate estrogen receptor activity, for example to treat or prevent breast cancer, to treat or prevent osteoporosis or to reduce the risk of cardiovascular disease in a subject (e.g., a postmenopausal female subject).

44 Claims, 3 Drawing Sheets

OTHER PUBLICATIONS

Hermenegildo, C. and Cano, A. 2000). "Pure Anti–Oestrogens," *Hum. Reprod. Update* 6(3):237–243.

Herrington, D.M. et al. (Jun. 2000). "Cardiovascular Effects of Droloxifene, a New Selective Estrogen Receptor Modulator, in Healthy Postmenopausal Women," *Arterioscler. Thromb. Vasc. Biol.* 20:1606–1612.

Ibrahim, N.K. and Hortobagyi, G.N. (Aug. 1999). "The Evolving Role of Specific Estrogen Receptor Modulators," *Surg. Oncol.* 8(2):103–123.

Johnston, S.R.D. et al. (Aug. 1, 1999). "Idoxifene Antagonizes Estradiol–dependent MCF–7 Breast Cancer Xenograft Growth through Sustained Induction of Apoptosis," *Cancer Res.* 59:3646–3651.

Jordan, V.C. (Jan.–Feb. 2000). "Antiestrogens: Clinical Applications of Pharmacology," *J. Soc. Gynecol. Investig.* 7(1) (Supplement):S47–S48.

Labrie, F. et al. (1999). "EM–652 (SCH 57068), A Third Generation SERM Acting as Pure Antiestrogen in the Mammary Gland and Endometrium," *J. Steroid Biochem. Mol. Biol.* 69:51–84.

Levenson, A.S. and Jordan, V.C. (1999). "Selective Oestrogen Receptor Modulation: Molecular Pharmacology for the Millenium," *Eur. J. Cancer* 35(14):1974–1985.

Love, R.R. et al. (Oct. 19, 1994). "Effects of Tamoxifen on Cardiovascular Risk Factors in Postmenopausal Women After 5 Years of Treatment," *J. Natl. Cancer Inst.* 86(20):1534–1539.

McDonnell D.P. (Jan.–Feb. 2000). "Selective Estrogen Receptor Modulators (SERMs): A First Step in the Development of Perfect Hormone Replacement Therapy Regimen," *J. Soc. Gynecol. Investig.* 7(1 Suppl):S10–S15.

Meunier, P.J. et al. (1999). "Treatment of Postmenopausal Women with Osteoporosis or Low Bone Density with Raloxifene," *Osteoporos. Int.* 10:433.

Minton, S.E. (Feb. 2000). "Chemoprevention of Breast Cancer in the Older Patient," *Hematol. Oncol. Clin. North Am.* 14(1):113–130.

Novotný, L. et al. (2000). "Tamoxifen in Cancer Therapy: Minireview," *Neoplasma* 47(1):3–7.

Plouffe L., Jr. (Jan.–Feb. 2000). "Selective Estrogen Receptor Modulators (SERMs) in Clinical Practice," *J. Soc. Gynecol. Investig.* 7(1 Suppl):S38–S46.

Roe, E.B. et al. (2000). "Selective Estrogen Receptor Modulators and Postmenopausal Health," *Adv. Intern. Med.* 45(Chapter 8):259–278.

Sun, J. et al. (1999). "Novel Ligands that Function as Selective Estrogens or Antiestrogens for Estrogen Receptor–$\alpha$ or Estrogen Receptor–$\beta$," *Endocrinol.* 140(2):800–804.

Tonetti, D.A. and Jordan, V.C. (1999). "The Estrogen Receptor: A Logical Target for the Prevention of Breast Cancer with Antiestrogens," *J. Mammary Gland Biol. Neoplasia* 4(4):401–413.

Yao, K. and Jordan, V.C. (1998). "Questions about Tamoxifen and the Future Use of Antiestrogens," *Oncologist* 3:104–110.

Tanase, T. et al., (1996) Assembly of carbohydrates on a nickel (II) center by utilizing N–glycosidic bond formation with tris(2–aminoethyl)amine (tren). Syntheses and characterization of [Ni{N–aldosyl)–tren](H$_2$O)]$^{2+}$, [NI{N,N'–bis(aldosyl)–tren}]$^{2+}$[Ni{N,N',N''–tris(aldosyl)–tren}]$^{2+}$ *Inorg. Chem.* 35:4848–4857.

Tanase, T. et al., (1997) "Peroxo–bridged dinuclear cobalt(III) complexes containing N–glycoside ligands from tris(2–aminoethyl)amine and D–glucose and their reversible dioxygen binding properties" *Chem. Commun.* 21:2115–2116.

Alley, M.C. et al. (1988). "Feasibility of Drug Screening with Panels of Human Tumor Cell Lines Using a Microculture Tetrazolium Assay," *Cancer Research* 48:589–601.

Asam, M.R. et al. (1997). "Tandem Mass Spectrometry of Alkali Cationized Polysaccharides in a Quadrupole Ion Trap," *J. Am. Soc. Mass. Spectrom.* 8:987–995.

Bundgaard, H. et al. (1989). "A Novel Solution–Stable, Water–Soluable Prodrug Type for Drugs Containing a Hydroxyl or an NH–Acidic Group," *Journal of Medicinal Chemistry* 32(12):2503–2507.

Fura, A. et al. (1993). "Differentiation of $Ca^{2+}$– and $Mg^{2+}$–Coordinated Branched Trisaccharide Isomers: An Electrospray Ionization and Tandem Mass Spectrometry Study," *Analytical Chemistry* 65(20):2805–2811.

Gaucher, S.P. et al. (1998). "Stereochemical Differentiation of Mannose, Glucose, Galactose, and Talose Using Zinc(II) Diethylenetriamine and ESI–Ion Trap Mass Spectrometry," *Analytical Chemistry* 70(14):3009–3014.

Graumann, K. et al. (2000). "Agonistic and Synergistic Activity of Tamoxifen in a Yeast Model System," *Biochem. Pharmacol.* 59(2):177–185.

Gupta, M. et al. (1988). "Estrogenic and Antiestrogenic Activities of 16alpha– and 2–hydroxy Metabolites of 17beta–Estradiol in MCF–7 and T47D Human Breast Cancer Cells," *J. Steroid Bicohem. Mol. Biol.* 67(5–6):413–419.

Hofmeister, G.E. et al. (1991). "Linkage Position Determination in Lithium–Cationized Disaccharides: Tandem Mass Spectrometry and Semiempirical Calculations," *J. Am. Chem. Soc.* 113(16):5964–5970.

Kissman, H.M. et al. (1957). "The Synthesis of Certain 5–Deoxy–D–ribofuranosylpurines," *J. Am. Chem. Soc.* 79:5534–5540.

Kissman, H.M. et al. (1958). "5–Deoxy–5–fluoro–D–ribofuranosyl Derivatives of Certain Purines, Pyrimidines and 5,6–Dimethylbenzimidazole," *J. Am. Chem. Soc.* 80:5559–5564.

Lammers, H. et al. (1994). "Reductive Amination of Aldohexoses with Mono– and Bifunctional Alkyl Amines: Conversion of Carbohydrates into EDTA Type Complexing Agents," *Tetrahedron* 50(27):8103–8116.

Ledl, F. et al. (1990). "New Aspects of the Maillard Reaction in Foods and in the Human Body," *Angewandte Chemie* (English Edition) 29(6):565–594.

Li, L.H. et al. (1979). "Comparative Biological and Biochemical Effects of Nogalamycin and Its Analogs on L1210 Leukemia," *Cancer Research* 39:4816–4822.

MacLeod, J.M. (1979). "Synthesis and Hydrolysis of N,N'–Diglycopyranosylethylenediamines," *Carbohydrate Research* 75:71–81.

Micheel, F. et al. (1956). "Glucose Derivatives of Proteins," In *Chemical Abstracts* (Feb. 25, 1957) 51(4):2556–2557.

Mitts, E. et al. (1944). "The Reaction of Glucose with Some Amines," *J. Am. Chem. Soc.* 66:483–486.

Morrison, R.H. et al. (1992). "Chapter 35: Carbohydrates II. Disaccharides and Polysaccharides," In *Organic Chemistry, Sixth Edition.* Farrell, D. et al., eds. Prentice Hall: New Jersey, pp. v–xxii, 1185–1204.

Patil, S.L. et al. (1989). "Synthesis and Biological Evaluation of 2–Desamino–2–methyl–$N^{10}$–propargyl–5,8–dideazafolic Acid and Related Compounds," *Journal of Medicinal Medicine* 32:1284–1289.

Silverstein, R.M. et al. (1991). "Apendix F: Proton Spin–Coupling Constants," In *Spectrometric Identification of Organic Compounds, Fifth Edition.* Sawicki, D. ed. John Wiley & Sons, Inc.:New York, pp. ix–x, 221.

Smith, G. et al. (1997). "Stereoselective β–Hydrogen Elimination from Nickel(II)–N–Glycoside Complexes," *Journal of Organic Chemistry* 62:2152–2154.

Verheyden, J.P.H. et al. (1974). "Synthesis of Some 4',5'–Unsaturated Pyrimidine Nucleosides," *Journal of Organic Chemistry* 39(24):3573–3579.

Weiskopf, A.S. et al. (1997). "Characterization of Oligosaccharide Composition and Structure by Quadrupole Ion Trap Mass Spectrometry," *Rapid Communications in Mass Spectrometry* 11:1493–1504.

Weiss, M.J. et al. (1959). "The Reaction of Periodate with Aminosugars. Anomalous Overoxidations of Aminofuranosides," *J. Am. Chem. Soc.* 81(15):4050–4054.

Yano, S. (1988). "Coordination Compounds Containing Sugars and their Derivatives," *Coordination Chemistry Reviews* 92:113–156.

Yano, S. et al. (1993). "Stereochemistry of Sugar Units in Glycosylamine Ligands of Octahedral Complexes Derived from Tris (trimethylenediamine)–Nickel(II) and Natural Aldohexoses," *J. Chem. Soc. Dalton Trans.* 1699–1706.

US 6,531,454 B1

GLYCOSYLATED POLYAMINES AND METHODS OF USE THEREFOR

RELATED APPLICATIONS

This application is a continuation-in-part application of U.S. Ser. No. 09/524,729, filed Mar. 14, 2000, now U.S. Pat. No. 6,420,344, which claims the benefit of U.S. Provisional Application No. 60/124,559 filed Mar. 16, 1999, the entire contents of which are hereby incorporated by reference.

STATEMENT OF RIGHTS TO INVENTIONS MADE UNDER FEDERALLY SPONSORED RESEARCH

This invention was made with Government support under grant No. GM 47356, awarded by the National Institutes of Health. The Government may have certain rights in this invention.

TECHNICAL FIELD

The present invention relates to certain sugars. More specifically, this invention provides glycosylated polyamine compounds, methods for their synthesis, characterization, their use as ligands in preparing metal complexes for developing analytical methodology, and their pharmaceutical uses, for example, as antitumor agents or modulators of estrogen receptor activity.

BACKGROUND OF THE INVENTION

Glycosylated amines, also variously known as N-glycosides, glycosylamines, or aminoglycosides, are formed by reacting a carbonyl containing sugar molecule with an amine. Glycosylated amines are known in the fields of polymer chemistry, and cosmetics. For example, glycosylated amines from primary amines of intermediate molecular weight have been reported to be good wetting agents. Mitts, E. and Hixon, R. M., *J. Am. Chem. Soc.*, 66: 483 (1944). Glycosylated amines as a class have been reported as components for detergents and cosmetics, surfactants, polymers, sweeteners and as liquid crystalline compounds. Lammers, et al., *Tetrahedron*, 59: 8103 (1994). Glycosylamines also have been used in kraft pulping liquor in the wood processing industry. MacLeod, J. M., *Carbohydrate Res.*, 75: 71 (1979).

Glycosylated amines also play a vital role at the cellular level, because they are essential components of nucleic acids, wherein the ring nitrogen atoms of purine or pyrimidine bases form N-glycosyl linkages with carbon atom 1 of D-ribose or 2-deoxy-D-ribose, which are incorporated into ribonucleic acid (RNA) and deoxyribonucleic acid (DNA), respectively. While the physiological functions of some of the glycosylated amines appear to have been examined, their potential as pharmacological agents has not been fully explored.

Lammers et al. supra, have disclosed the preparation of mono- and diglycosylamines, wherein the amine and the saccharide were mixed in water under reductive amination conditions. However the yields were poor. Mitts et al. supra, reported the preparation of N,N'-propylenediglucamine by refluxing glucose with propylenediamine in methanol followed by reduction over activated Raney Nickel and at high pressures and temperatures. The yield appeared to be very low in this case also because it was reported that only a very small amount of the reduced compound was isolated. Mitts et al. further disclosed that attempts to isolate and characterize the condensation products of amines such as isopropylamine, 2-aminooctane, and propylenediamine with glucose were not successful. Accordingly, there exists a need for a synthetic procedure to prepare glycosylated amines and glycosylated polyamines comprising a variety of sugars and amines.

Many analytical techniques have been developed to characterize glycosylamines. Only recently, however, has the research focussed on investigation of linkage information of metal cationized oligosaccharides by mass spectrometry (MS) and tandem mass spectrometry ($MS^n$). Asam, M. R. and Glish, G. L., *J. Am. Soc. Mass Spectrom.*, 8: 987 (1998); Weiskopf, et al. *Rapid Com. Mass Spec.*, 11: 1493 (1997); Hofineister, et al., *J. Am. Chem. Soc.*, 113: 5964 (1991); and Fura, A. and Leary, J. A., *Anal. Chem.*, 65: 2805 (1993).

Mass spectrometry is not a tool traditionally used to distinguish stereoisomers. However, the stereochemistry of individual monosaccharides as well as α versus β configuration of glycosidic bonds in disaccharides can be determined by $MS^n$. See for example, Gaucher, S. P. and Leary, J. A., *Anal. Chem.*, 70: 3009 (1998); Smith, et al. *J. Org. Chem.*, 62: 2152 (1997). This method involves cationizing the saccharide using a metal-ligand system such as $Zn(diethylenetriamine)_2Cl_2$ or $Ni(1,3-diaminopropane)_3Cl_2$, by allowing metal N-glycoside complexes to form in solution. Yano, S., *Coord. Chem. Rev.*, 92: 113 (1988); and Yano, et al. *J. Chem. Soc., Dalton Trans.*, 1699 (1993). The complexes are then transferred from solution to the gas phase by electrospray ionization (ESI) or fast atom bombardment (FAB) and analyzed by tandem mass spectrometry (MS/MS). See for example, Gaucher and Leary, supra; Smith and Leary, supra; and Smith, et al., supra. The axial versus equatorial stereochemistry of the C2 and C4 hydroxyl groups could be differentiated by the cross ring cleavage patterns observed in the gas phase.

In the above-described mass spectrometric procedures, it is time consuming to screen the efficacy of different metals for a given saccharide or ligand because each individual metal-ligand complex requires synthesis a priori. Accordingly, methods for rapid synthesis of metal-ligand complexes are needed so that the metal-ligand complexes so formed can be readily analyzed upon their synthesis.

All literature references, patents, and patent applications cited in this specification are hereby incorporated by reference in their entirety.

DISCLOSURE OF THE INVENTION

The present invention discloses glycosylated polyamines, methods for their preparation and use, and pharmaceutically acceptable compositions comprising gylcosylated polyamines. Glycosylated polyamines, in one embodiment, are prepared from two or more saccharides and a polyamine. In one embodiment, the glycosylated polyamine compound has the following formula (Formula I):

(Formula I)

wherein:

each of $R_1$ and $R_2$ is independently a monosaccharide residue or an oligosaccharide residue; Z is an aliphatic polyamino linker that is the residue of an aliphatic polyamine comprising at least two amino groups, each of which is independently a primary or secondary amino group; and each of $R_1$ and $R_2$ is linked through its anomeric carbon at its 1 position to a different amino group of the aliphatic polyamino linker to form a glycosidic bond;

provided that when each of $R_1$ and $R_2$ is the same and is a glucose, galactose, mannose, or cellobiose residue, Z is the residue of an aliphatic polyamine other than ethylenediamine or diaminopropane;

and pharmaceutically acceptable salts, prodrugs and derivatives thereof.

In one embodiment, each of $R_1$ and $R_2$ of Formula I is an oligosaccharide residue. In another embodiment, at least one of $R_1$ and $R_2$ has a group other than hydrogen in equatorial conformation at the C2 position that is adjacent to the anomeric carbon atom linked to the aliphatic polyamine.

In a further embodiment, the group in equatorial conformation at C2 position is a hydroxy, alkoxy, halo, lower alkyl, amino, N-acetyl, N-alkyl, N-hydroxy, N-alkoxy, aminothiol, amino alcohol, spermine, or nitro group, and optionally a hydrogen in the axial conformation.

In one embodiment of Formula I, $R_1$ is a monosaccharide residue and $R_2$ is an oligosaccharide residue. In another embodiment, each of $R_1$ and $R_2$ of Formula I is a monosaccharide residue. In yet another embodiment, each of $R_1$ and $R_2$ of Formula I is a hexose residue. In a further embodiment, each of the hexose residues is independently substituted by one or more of the following groups: a lower alkyl, lower alkoxy, acyl, carboxy, carboxyamino, amino, acetamido, halo, thio, or nitro; provided that the anomeric carbon has a free hydroxyl group to form a glycosidic linkage with the aliphatic polyamino linker.

In one embodiment, at least one of $R_1$ and $R_2$ has a group other than hydrogen in equatorial conformation at the C2 position that is adjacent to the anomeric carbon atom linked to the aliphatic polyamine. In another embodiment, the group in equatorial conformation at C2 position is a hydroxy, alkoxy, halo, lower alkyl, amino, N-acetyl, N-alkyl, N-hydroxy, N-alkoxy, or nitro group, and optionally a hydrogen in the axial conformation.

In one embodiment, the aliphatic polyamino linker of Formula I is a residue of diethylenetriamine. In a further embodiment, the diethylenetriamine residue is substituted by one or more the following groups: lower alkyl, hydroxy, lower alkoxy, amino, acyl, acetamido, halo, or nitro; provided that there is at least one amino group per each saccharide residue to form a glycosidic linkage.

Another embodiment presents a compound of Formula I, wherein each of $R_1$ and $R_2$ is the same and is a glucose, galactose, allose or fucose residue and the aliphatic polyamine linker is the residue of diethylenetriamine. Some specific embodiments include: diglucosyl-diethylenetriamine; digalactosyl-diethylenetriamine; diallosyl-diethylenetriamine; and difucosyl-diethylenetriamine; and their pharmaceutically acceptable salts, prodrugs and derivatives. One such salt may be HCl salt.

Pharmaceutically acceptable compositions comprising glycosylated polyamines, such as a compound of Formula I and pharmaceutically acceptable salts, prodrugs and derivatives thereof are also provided.

Glycosylated polyamine compounds, for example, of formula I, are effective as anticancer agents. Such anticancer activity may include inhibition of tumor cell growth, or multiplication or tumor size. Some examples of such compounds are diglycosylated diethylenetriamines, such as diglucosyl diethylenetriamine, digalactosyl diethylenetriamine, difucosyl diethylenetriamine, and diallosyl diethylenetriamine.

Accordingly, compounds of Formula I can be employed in methods to treat cancers or tumors. Such methods include providing one or more compounds of Formula I, their pharmaceutically effective salts, prodrugs and derivatives in an effective amount to treat a cancer or reduce the tumor cell growth or multiplication or tumor size. Exemplary cancers that may be treated include: leukemia, non-small-cell lung cancer, small-cell lung cancer, colon cancer, a cancer of the central nervous system, melanoma, ovarian cancer, breast cancer, renal and prostate cancer. The above-described compounds of Formula I can also be used in preparing one or medicaments to treat one or more of such cancers.

Furthermore, the compounds of the invention can be used as modulators of the estrogen receptor (ER), for example to modulate an estrogen receptor-mediated response. Based on crystallographic studies of their structure, compounds of the invention are predicted to interact with (bind to) the estrogen receptor and thus can be used to modulate ER activity, for example in a variety of conditions, disorders or diseases involving estrogen-mediated activities. In addition to treatment of hormonally-regulated cancers, such as breast cancers, such conditions, disorders and/or diseases include, for example, preventing, treating or delaying onset of osteoporosis, preventing or delaying onset of breast cancer in high risk women, modulation of ovulation (e.g., ovulation induction), preventing, treating or delaying onset of cardiovascular disorders (e.g., reduction of cholesterol levels), preventing, treating or delaying onset of uterine disorders (e.g., endometriosis, dysfunctional uterine bleeding, fibroids), and overall management of postmenopausal women's health. A preferred compound for modulation of ER activity is diglucosyl diethylenetriamine (also referred to herein as SPG-20).

One specific embodiment of Formula I is diglucosyl diethylenetriamine. The diglucosyl diethylenetriamine can be prepared, for example, in a salt form such as HCl salt, which has the structure:

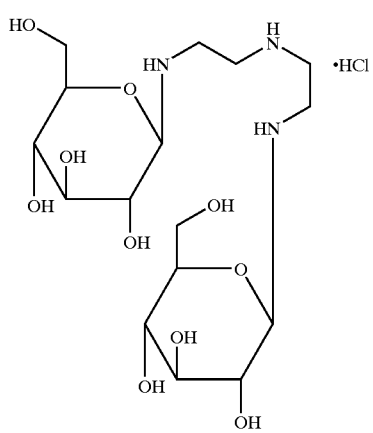

1

Yet another specific embodiment of Formula I is digalactosyl diethylenetriamine. The digalactosyl diethylenetriamine can be prepared, for example, in a salt form, such as HCl salt, which has the structure:

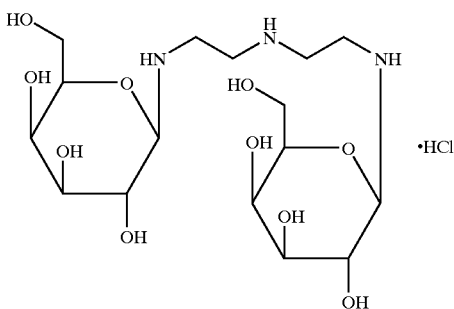

2

Another specific embodiment of Formula I is difucosyl diethylenetriamine. The difucosyl diethylenetriamine can be prepared, for example, in a salt form, such as HCl salt, which has the structure:

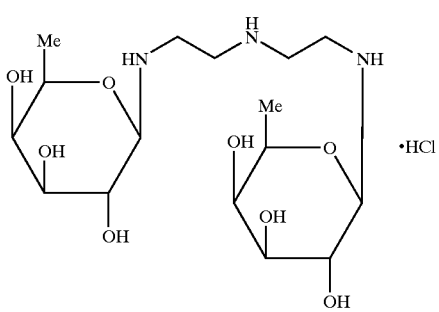

3

Another specific embodiment of Formula I is diallosyl diethylenetriamine. The diallosyl diethylenetriamine can be prepared, for example, in a salt form such as HCl salt, which has the structure:

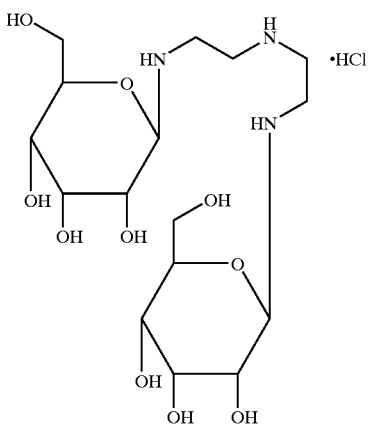

4

The present invention also provides a metal-polyamine-N-glycosyl complex of Formula II:

[R₁—Z—R₂].Y  (Formula II)

wherein in one embodiment, [R₁—Z—R₂] is represented by Formula I; and Y is a metal compound; and pharmaceutically acceptable salts, prodrugs and derivatives thereof.

In one embodiment, each of R₁ and R₂ is a hexose residue. In yet another embodiment, each of R₁ and R₂ is the same and is a glucose, galactose, allose or fucose residue.

In one embodiment of Formula II, Z is an aliphatic polyamino linker which is a residue of a polyamine selected from the group consisting of ethylene diamine, propylene diamine, diethylene triamine. In an embodiment of Formula II, the metal compound Y is a metal such as zinc, or a metal salt such as zinc chloride, zinc acetate, zinc triflate, sodium chloride magnesium chloride, copper chloride, cobalt chloride, nickel chloride, or calcium carbonate. In addition, the metal salts can be also those of organic origin such as sulfonate triflate or tosylate.

An embodiment of a glycosylated polyamine-zinc complex is N,N'-dihexosyldiethylenetriamine-zinc chloride which has the following structure:

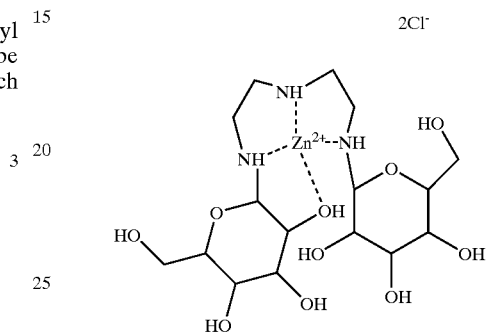

In one embodiment, a method for preparing a metal-polyamine-N-glycosyl complex, for example, of Formula II:

[R₁—Z—R₂].Y                              Formula II is provided which comprises:

a) providing a glycosylated polyamine compound, for example, of Formula I, [R₁—Z—R₂]; b) reacting the compound of Formula I with a metal compound, Y, and a salt, such as ammonium hydroxide, in a solvent, such as methanol, to form a metal complex having the formula, Formula II, [R₁—Z—R₂].Y; and, optionally, c) isolating the metal complex obtained in step b).

The metal compound Y and the compound of Formula I are preferably reacted in about equimolar amounts.

In one embodiment, the metal compound comprises a metal, such as zinc, or a metal salt, such as zinc chloride. An exemplary general reaction scheme to prepare a zinc chloride-diethylenetriamine-dihexosyl complex is shown below:

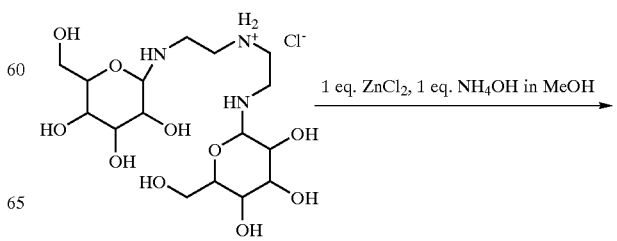

-continued

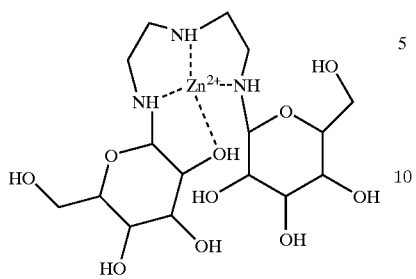

2Cl⁻

The present invention also provides an analytical method to determine the stereospecificity of a glycosidic linkage between two sugars in a disaccharide. The method comprises the steps of: a) providing a glycosylated polyamine, for example, of Formula I, wherein at least one of $R_1$ and $R_2$ is a disaccharide; b) cationizing the glycosylated polyamine using a metal compound Y to form the corresponding metal-polyamine-N-glycoside complex of Formula II; c) ionizing the metal-polyamine-N-glycoside complex; and d) detecting the ions characteristic of a particular stereospecific linkage of the disaccharide using one or more mass spectrometers.

In one embodiment, the metal compound Y comprises zinc chloride or nickel chloride. In another embodiment, the metal-polyamine-glycoside complex is ionized through an electrospray ionization or a fast atom bombardment ionization technique. In yet another embodiment, the ion detection is accomplished by using two or more mass spectrometers arranged in tandem, in space and time, for example as triple quad instruments or those employing ion trap or ion cyclotron resonance technology.

The present invention also discloses a method for detecting the presence of an axial or equatorial conformation of a group, for example, at the C2 position of a saccharide, which method comprises the steps of: a) reacting an aliphatic polyamine and the saccharide in the presence of a precipitating agent; b) observing for a precipitate in the reaction mixture within a certain time, such as from within a few minutes to within a few hours, for example, 3–8 hours; and c) noting the presence of equatorial conformation of the group at the C2 position if a precipitate is observed in step b).

In one embodiment, the aliphatic polyamine and the saccharide are reacted at a certain ratio, for example, at about a 1:2 molar ratio. In another embodiment, the precipitating agent is present in about 1 molar concentration. In some embodiments, the precipitate can be observed within a few minutes, whereas in certain other embodiments, the precipitate is formed within a few hours; provided that the saccharide has an equatorial substitution at the C2 position.

In one embodiment, the substituent at the C2 position is a hydroxyl group. Other examples of substituents at the C2 position include alkoxy, halo, lower alkyl, amino, substituted amino, and nitro groups. The saccharide may be for example, a monosaccharide such as a pentose, or hexose, or an oligosaccharide. The precipitating agent can be any acidic salt that provides a halo counterion, for example, HCl, HBr, HI. Preferably, the counterion is a chloro ion. The aliphatic polyamine includes polyamines such as diethylene triamine, triethylenetetramine, ethylene diamine, and diaminopropane.

DETAILED DESCRIPTION OF THE INVENTION

Figure 1:
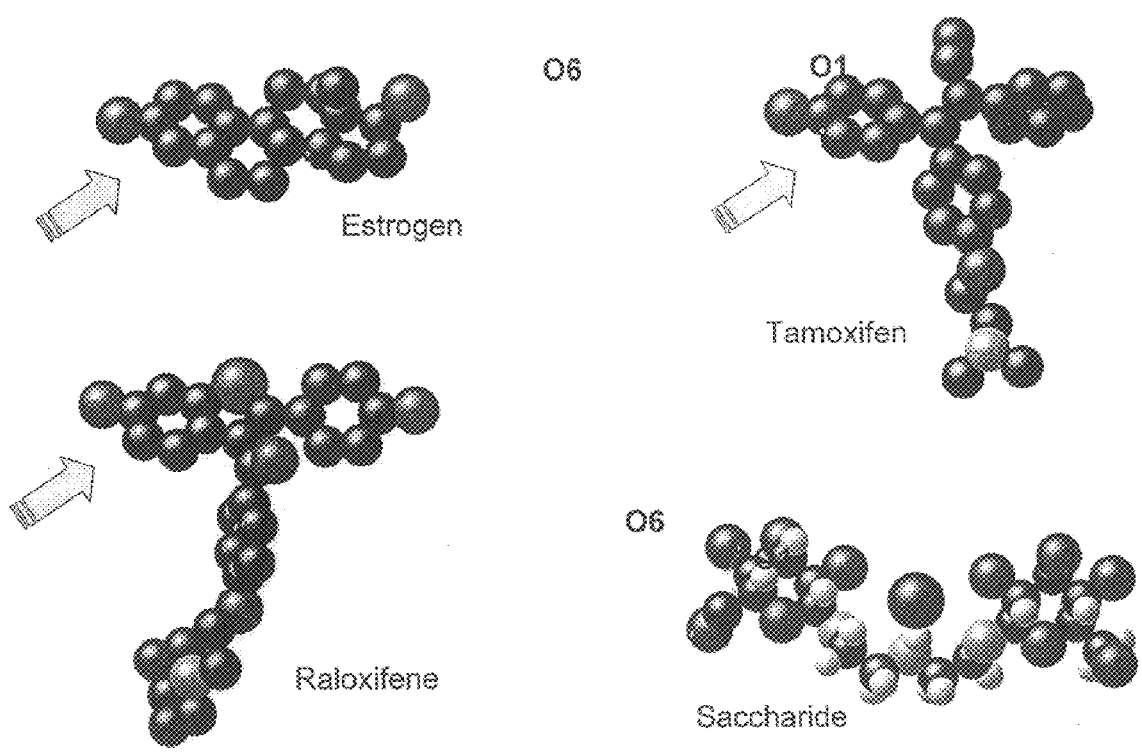
FIG. 1 is a comparison of the crystal structures of estrogen, tamoxifen, raloxifene and diglucosyl diethylenetriamine (SPG-20), showing similarities in molecular size.

The present invention provides glycosylated polyamines, methods for their synthesis and methods of using them, for example, as anticancer agents. Metal complexes of glycosylated polyamines, the preparation of such metal complexes, and analytical methods using the metal complexes are also provided. Methods for detecting equatorial and axial conformations of a group other than hydrogen at the C2 position of a saccharide molecule also are provided.

Glycosylated Polyamine Compounds

This invention provides a compound of the formula (Formula I):

$R_1$—Z—$R_2$ (Formula I)

wherein in one aspect, each of $R_1$ and $R_2$ is independently a saccharide residue, such as a monosaccharide residue or an oligosaccharide residue; Z is a polyamino linker that is the residue of a polyamine comprising at least two amino groups, each of which is independently a primary or secondary amino group; and each of $R_1$ and $R_2$ is linked through its anomeric carbon at its 1 position to a different amino group of the polyamino linker to form a glycosidic bond; provided that when both $R_1$ and $R_2$ are the same and represent glucose, galactose, mannose, or cellobiose residues, Z is a residue of a polyamine other than ethylenediamine or diaminopropane; and pharmaceutically acceptable salts, prodrugs and derivatives thereof.

In Formula I, each of $R_1$ and $R_2$ can independently represent the same saccharide residue or residues of different saccharides. For example, $R_1$ and $R_2$ can both be monosaccharide residues or $R_1$ can be a monosaccharide residue and $R_2$ can be an oligosaccharide residue, or vice versa. Further, each of $R_1$ and $R_2$ can be independently a monosaccharide residue such as a pentose, hexose or heptose residue. Thus, $R_1$ can be a pentose residue and $R_2$ can be a hexose residue.

The term "saccharide residue" as used herein, refers to the portion of a saccharide that is without a hydroxyl group at the reducing end (C1) of the saccharide. The saccharide residue is thus the portion of the saccharide attached to the polyamine. Such structures may also be referred to as saccharyl. Thus, for example, the phrases "glucose residue" and "glucosyl" refer to the same glucose structure which lacks a hydroxyl group at its reducing end (C1). Similarly, "polyamine residue" refers to the polyamino portion of the glycosylated polyamine that is bonded to various saccharide residues. These terms are readily understood by one of ordinary skill in the art. This terminology can also be illustrated from the following structure of compound 1, wherein each of $R_1$ and $R_2$ represents, for example, glucosyl or a glucose residue and Z represents a polyamine residue:

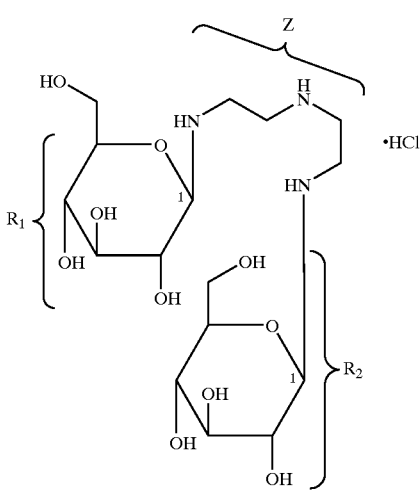

Exemplary monosaccharide residues include residues of a pentose, hexose, or a heptose. Non-limiting examples of pentoses include arabinose, ribose, ribulose, xylose, lyxose, and xylulose. Non-limiting examples of hexoses include glucose, galactose, fructose, facose, mannose, allose, altrose, talose, idose, psicose, sorbose, and tagatose. Non-limiting examples of heptoses include mannoheptulose and sedoheptulose.

Some saccharide residues may have a hydroxyl group at the C2 position in an axial or equatorial conformation. For example, glucosyl residue has a hydroxyl group in equatorial conformation at its C2 position, whereas a mannosyl residue, for example, has a hydroxyl group in axial conformation at its C2 position.

In some cases, the saccharide residue may possess a group other than a hydrogen or hydroxyl at its C2 position. Some examples of groups that may be present at the C2 position include groups such as alkoxy, halo, lower alkyl, amino, N-acetyl, N-alkyl, N-hydroxy, N- alkoxy, aminothiol, amino alcohol, spermine, or nitro group. Such groups may be present in equatorial or axial conformation at the C2 position.

The saccharides of the present invention may also be substituted with various groups. Such substitutions may include lower alkyl, lower alkoxy, acyl, carboxy, carboxyamino, amino, acetamido, halo, thio, nitro, keto, and phosphatyl groups, wherein the substitution may be at one or more positions on the saccharide, except for the anomeric carbons which form the glycosidic bond. Moreover, the saccharides may also be present as a deoxy saccharide. Examples of such substituted saccharides include: D-glucosamine and D-galactosamine, which are 2-amino-2-deoxy glucose and 2-amino-2-deoxy galactose, respectively. Examples of carboxy-containing saccharides include aldonic, aldaric, and uronic acids. Examples of carboxy-containing amino sugars include N-acetylmuramic acid and N-acetylneuraminic acid, wherein each is a six-carbon amino sugar linked to a three-carbon sugar acid.

Preparation of substituted sugars with the above-listed substituents is well within the ordinary skill in the art. General methods for preparing substituted sugars have been described in, for example, U.S. Pat. No. 5,874,413; Kissman et al., "5-deoxy-5-fluoro-D-ribofuranosyl derivatives of certain purines, pyrimidines and 5,6-dimethylbenzimidazole" J. Chem. Soc. (1958); 80:5559–5564; Kissman et al., "The synthesis of certain 5-deoxy-D-ribofuranosylpurines" J. Am. Chem. Soc. (1957) 79:5534–5540; Weiss et al., "The reaction of periodate with aminosugars. Anomalous overoxidations of aminofuranosides" J. Am. Med. Soc.(1959) 81:4050–4054; Verheyden et al., "Halo sugar nucleosides. IV. Synthesis of some 4'5'-unsaturated pyrimidine nucleosides" J. Org. Chem. (1974); 39:3573–3579.

Saccharides exist as stereoisomers, optical isomers, anomers, and epimers. The meaning of saccharide as used herein encompasses such isomers, anomers and epimers. Thus, a hexose for example can be either an aldose or a ketose, and can be of D- or L-configuration, can assume either an alpha or beta conformation, and can be a dextro- or levo-rotatory with respect to plane-polarized light.

An oligosaccharide includes two or more monosaccharides joined through glycosidic linkage. An oligosaccharide may result from a glycosidic linkage between, for example, a hexose and another hexose or between a pentose and a hexose. An oligosaccharide of this invention may comprise of 2–6 saccharyl units, preferably, 2–4 saccharyl units, and more preferably, 2–3 saccharyl units.

Nonlimiting examples of oligosaccharides include lactose, maltose, cellobiose, gentiobiose, melibiose, isomaltose, mannobiose and xylobiose. The oligosaccharides have a free anomeric carbon to form glycosidic linkage with the polyamine. The preparation of several oligosaccharides is well-known in the art. They can be obtained by partial hydrolysis of polysaccharides or synthesized from the desired monosaccharides. See for example, Morrison & Boyd, Organic Chemistry, Prentice-Hall, Chapter on Carbohydrates, latest edition. In addition, several oligosaccharides can be purchased from commercial sources or can be custom made using ordinary skill in the art.

Oligosaccharides also exist in many isomeric, epimeric and anomeric forms and the oligosaccharides described herein include such isomeric, epimeric and anomeric forms.

In one aspect, each of $R_1$ and $R_2$ of Formula I is an oligosaccharide residue. In some cases, at least one of $R_1$ and $R_2$ has a group other than hydrogen in equatorial conformation at the C2 position that is adjacent to the anomeric carbon atom linked to the aliphatic polyamine. In some other cases, each of $R_1$ and $R_2$ has a group other than hydrogen in equatorial conformation at that C2 position. The group in equatorial conformation at C2 position may be a hydroxy, alkoxy, halo, lower alkyl, amino, N-acetyl, N-alkyl, N-hydroxy, N-alkoxy, aminothiol, amino alcohol, spermine, or nitro group.

In one aspect, in Formula I, $R_1$ is a monosaccharide residue and $R_2$ is an oligosaccharide residue. In another aspect of Formula I, each of $R_1$ and $R_2$ is a monosaccharide residue. In yet another aspect of Formula I, each of $R_1$ and $R_2$ is a hexose residue. Each of the hexose residues may be independently substituted by one or more of the groups: a lower alkyl, lower alkoxy, acyl, carboxy, carboxyamino, amino, acetamido, halo, thio, or nitro; provided that the anomeric carbon has a free hydroxyl group to form a glycosidic linkage with the aliphatic polyamino linker.

In some cases, at least one of $R_1$ and $R_2$ has a group other than hydrogen in equatorial conformation at the C2 position that is adjacent to the anomeric carbon atom linked to the aliphatic polyamine. In some other cases, each of $R_1$ and $R_2$ has a group other than hydrogen in equatorial conformation at that C2 position. The group in equatorial conformation at C2 position may be a hydroxy, alkoxy, halo, lower alkyl, amino, N-acetyl, N-alkyl, N-hydroxy, N-alkoxy, aminothiol, amino alcohol, spermine, or nitro group.

"Aliphatic polyamine" refers to two or more amino groups separated by one or more carbon atoms representing an aliphatic group, wherein the amino groups can be primary, secondary or tertiary, provided that the amino group that is bonded to the anomeric carbon atom of a mono- or oligo-saccharide is either a primary or a secondary amine. Thus, the term "aliphatic polyamino linker" refers to the aliphatic polyamino group that links to one or more saccharides, wherein each saccharide, through its anomeric carbon at the 1 position, forms a glycosidic bond with a primary or secondary amino group of the aliphatic polyamine.

In one aspect, the aliphatic polyamino linker includes two or more amino groups and two or more carbons, for example from 4 to 10, provided that the aliphatic polyamino linker has at least two amino groups, wherein each amino group can independently be a primary or secondary amino group. Preferably, the aliphatic polyamino linker has 2–6 such amino groups, and more preferably, 2–4 such amino groups. Particular examples of aliphatic polyamines include ethylene diamine, diaminopropane, diethylenetriamine and triethylenetetramine.

The aliphatic polyamine may be substituted at one or more positions on the aliphatic portion or on the amino portion, with the proviso that there be at least one primary or secondary amino group per saccharide residue (for example, $R_1$ and $R_2$ as described above) to be conjugated. For example, diethylenetriamine may be substituted by one or more the following groups: lower alkyl, hydroxy, lower alkoxy, amino, acyl, acetamido, halo, or nitro; provided that there is at least one primary or secondary amino group per each N-glycosidic linkage to be formed.

"Aliphatic" refers to a cyclic, branched, or straight chain group containing only carbon and hydrogen, such as methyl, pentyl, and adamantyl. Aliphatic groups can be unsubstituted, or may be substituted with one or more substituents, e.g., halogen, alkoxy, acyloxy, amino, hydroxyl, mercapto, carboxy, benzyloxy, phenyl, benzyl, or other functionality that may be suitably blocked, if desired, for example with a protecting group. Aliphatic groups can be saturated or unsaturated (e.g., containing —C═C— or —C≡C— subunits), at one or several positions. Typically, aliphatic groups will comprise 2 to 12 carbon atoms, preferably 2 to 8, and more preferably 2 to 5 carbon atoms.

The phrase "lower alkyl" refers to alkyls having 1–4 carbon atoms, such as methyl, ethyl, propyl or butyl. The phrase "substituted amino" refers to a primary amino group wherein each of the hydrogens may be independently replaced by groups such as lower alkyl, hydroxyl, alkoxyl, acyl groups such as —C(O)CH$_3$ or C(O)C$_2$H$_5$.

One specific example of a glycosylated polyamine is diglucosyl-diethylenetriamine, wherein each of $R_1$ and $R_2$ is glucosyl and the polyamino linker is a residue of diethylenetriamine. The diglucosyl-diethylenetriamine can be prepared in a salt form such as a HCl salt. The structure of diglucosyl-diethylenetriamine.HCl (1) is shown below:

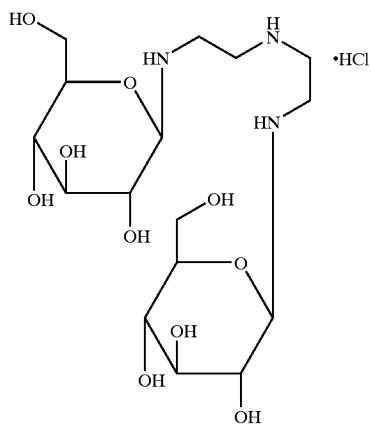

Another example of a glycosylated polyamine is digalactosyldiethylenetriamine, wherein each of $R_1$ and $R_2$ is galactosyl and the polyamino linker is a residue of diethylenetriamine. The digalactosyldiethylenetriamine can be prepared in a salt form, such as a HCl salt. The structure of digalactosyldiethylenetriamine.HCl (2) is shown below:

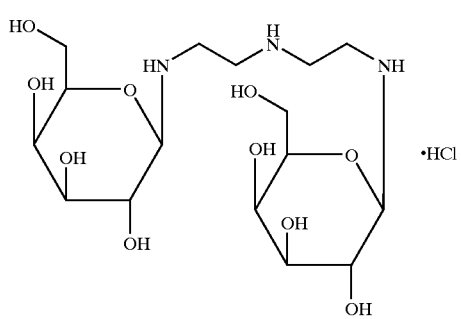

Another example of a glycosylated polyamine is difucolsyl-diethylenetriamine, wherein each of $R_1$ and $R_2$ is fucosyl and the polyamino linker is a residue of diethylenetriamine. The difucosyl-diethylenetriamine can be prepared in a salt form such as a HCl salt. The structure of difucosyl-diethylenetriamine.HCl (3) is shown below:

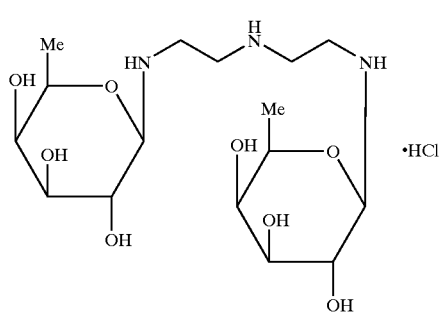

Yet another example of a glycosylated polyamine is diallosyl-diethylenetriamine, wherein each of $R_1$ and $R_2$ is allosyl and the polyamino linker is a residue of diethylenetriamine. The diallosyl-diethylenetriamine may be provided in a salt form, such as an HCl salt. The structure of diallosyl-diethylenetriamine.HCl (4) is shown below:

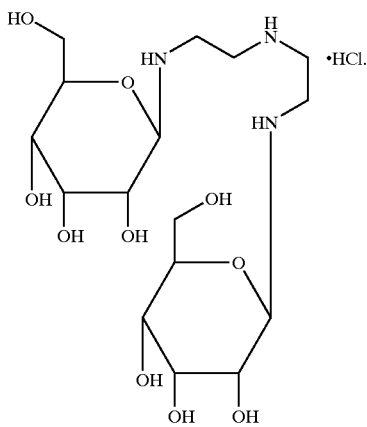

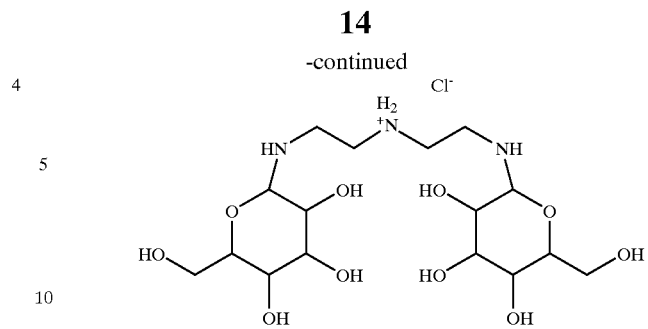

Diglycosylamines may be characterized by methods available in the art, such as, by $^{13}$C-NMR and mass spectra and X-ray crystallography. See for example, Lammers, et al, supra at 8105–8116; Gaucher and Leary, supra; Fura and Leary, supra; and Smith, et al, supra.

Methods of Preparation of Glycosylated Polyamines

The compounds of Formula I can be prepared by: a) combining an inorganic acid such as HCl with an aliphatic polyamine; and b) combining each of the saccharides corresponding to the $R_1$ and $R_2$ saccharide residues with the product obtained in step a) to form a glycosylated polyamine product; and optionally, c) isolating the glycosylated polyamine product of step b). Equimolar amounts of the inorganic acid, the polyamine and each of the saccharides may be used in the method.

The aliphatic polyamine is dissolved in an organic solvent such as methanol and kept at about 0° C. to room temperature. HCl is provided in a relatively nonpolar solvent such as diethylether. Step a) comprises adding HCl to the polyamine solution dropwise with stirring. In step b), the product of step a) is warmed up, if necessary, to room temperature, and each saccharide corresponding to the $R_1$ and $R_2$ saccharide residue in a polar solvent such as water is added to the product of step a). The reaction mixture is allowed to stir for at least an hour and the product is collected. Optionally, the reaction mixture is kept at 4° C. overnight and yields can be improved.

The isolation step c) also can include collecting the glycosylated polyamine product and drying under vacuum, and, optionally, dissolving the dried product in water, and recrystallizing in an organic solvent, such as a 50:50 mixture of methanol and ethanol.

As described above, each of $R_1$ and $R_2$ can represent a variety of saccharide residues while Z is an aliphatic polyamino linker. Some specific examples prepared by this method include diglucosyl diethylenetriamine, difucosyl diethylenetriamine, digalactosyl diethylenetriamine, and diallosyl diethylenetriamine.

A general reaction scheme for preparing a hexosyl diethylenetriamine, wherein both $R_1$ and $R_2$ are hexosyl, is illustrated below:

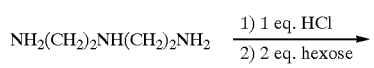

Thus, for example, about 1 mole of an inorganic acid such as HCl is combined with about 1 mole of an aliphatic polyamine. About 1 mole each of the saccharides corresponding to the saccharide residues represented by $R_1$ and $R_2$ is reacted with the above aliphatic polyamine.HCl mixture to form $R_1$—Z—$R_2$ product; which can be isolated.

When the two saccharyl groups (represented by $R_1$ and $R_2$), for example, are the same, such as glucosyl, the molar ratio of the saccharide to the polyamine is about 2:1. However, when the two saccharyl groups are different, i.e., when $R_1$ is, for example, a glucosyl and $R_2$ is, for example, a galactosyl, the ratio of glucose to galactose to polyamine is for example about 1:1:1. Thus, one mole of the polyamine reacts with one mole of each saccharide to form one mole of the glycosyl polyamine.

Applications

The compounds of the invention, based on their crystallographic structure, are capable of binding to the estrogen receptor and thus are predicted to be modulators of estrogen receptor activity. As described in Example 8, crystallographic studies of diglucosyl diethylenetriamine (SPG-20) demonstrate that it has structural similarity to estrogen and the selective estrogen receptor modulators tamoxifen and raloxifene. Binding of a compound to the estrogen receptor can lead to a variety of functional outcomes. Certain compounds, such as estrogen, act as receptor agonists. Other compounds, referred to as antiestrogens, act as receptor antagonists. Still other compounds, referred to as selective estrogen receptor modulators (SERMs), have antagonistic activity in certain tissues (e.g., breast and uterus) but have agonist activity in other tissues (e.g., bones, cardiovascular system and brain).

The agonist vs. antagonist properties of a compound (e.g., a glycosylated polyamine compound of the invention) can be tested using screening assays known in the art. For example, the effect of a test compound on the proliferation of hormone-responsive breast cancer cell lines (e.g., MCF-7 or T47D human breast cancer cells) can be determined, either alone or in the presence of 17beta-estradiol (ES). Mitogenic activity toward the breast cancer cells is indicative of ER agonist activity, whereas the ability to inhibit ES-mediated cell proliferation is indicative of ER antagonist activity. Additionally or alternatively, the effect of test compounds on the transactivation of an ER-responsive reporter gene (e.g., a reporter gene containing promoter inserts from the cathepsin D and creatine kinase B genes) can be assessed to determine agonist vs. antagonist activity (see e.g., Gupta, M. et al. (1998) *J. Steroid Biochem. Mol. Biol.* 67:413–419). Moreover, a yeast model system has been described in the art for assessing ER agonist vs. antagonist activity (see Graumann, K. and Jungbauer, A. (2000) *Biochem. Pharmacol.* 59:177–185). Given the structural similarity of SPG-20 to the SERMs tamoxifen and raloxifene, SPG-20 is predicted to also be a SERM, having both receptor antagonist and receptor agonist properties.

The compounds of the invention can be used to modulate estrogen receptor activity. Accordingly, in one aspect, the invention provides a method of modulating estrogen receptor activity comprising contacting an estrogen receptor with a compound of the invention such that estrogen receptor activity is modulated. This modulatory method of the invention can be carried out in vitro on cells in culture or, alternatively, in vivo by administering a compound of the invention to a subject.

Glycosylated polyamine compounds, for example, of formula I, are effective as anticancer agents. Such anticancer activity may include inhibition of tumor cell growth, or multiplication or tumor size. Some examples of such compounds are diglycosylated diethylenetriamines, such as diglucosyl diethylenetriamine, digalactosyl diethylenetriamine, difucosyl diethylenetriamine, and diallosyl diethylenetriamine. Thus, in one embodiment, the invention provides a method for inhibiting growth of cancer cells comprising contacting cancer cells with a compound of the invention such that growth of the cancer cells is inhibited. Preferred cancer cells include breast cancer cells, ovarian cancer cells, colon cancer cells and renal cancer cells. Other exemplary cancers that may be treated include: leukemia, non-small-cell lung cancer, small-cell lung cancer, a cancer of the central nervous system, melanoma and prostate cancer.

Accordingly, compounds of Formula I can be employed in methods to treat cancers or tumors. Such methods include providing one or more compounds of Formula I, their pharmaceutically effective salts, prodrugs and derivatives in an effective amount to treat a cancer or reduce the tumor cell growth or multiplication or tumor size. Exemplary cancers that may be treated include: leukemia, non-small-cell lung cancer, small-cell lung cancer, colon cancer, a cancer of the central nervous system, melanoma, ovarian cancer, breast cancer, renal and prostate cancer. The above-described compounds of Formula I can also be used in preparing one or imedicaments to treat one or more of such cancers.

Methods for assaying compounds for biological activity such as anti-cancer activity are well known in the art. See, for example, Li, L. H. et al., *Cancer Res.,* 39: 4816–4822 (1979)).

The glycosylated polyamine compounds of Formula I can be prepared in a pharmaceutically acceptable form, such as a salt suitable for a particular formulation or route of administration in a suitable dose and dosage form.

The glycosylated polyamine also may be in a prodrug or derivative form, i.e., as salts that are capable of being hydrolyzed or solvated under physiological conditions. Examples of such salts include sodium, potassium, and hemisulfate. The term "prodrug" is further intended to include lower hydrocarbon groups capable of being hydrolyzed or solvated under physiological conditions, e.g. methyl, ethyl, and propyl.

Prodrugs and derivatives may be prepared by modifying pharmacologically active molecules to enhance certain pharmaceutical characteristics such as oral absorption, plasma half-life, protein binding, or entry through blood-brain barrier. These modified molecules are in general, though not invariably, inactive by themselves, but release the active molecule in vivo upon being acted on by enzymes or chemicals or physiological conditions in vivo. These prodrugs and derivatives are known in the medicinal art. See for example, Bundgaard et al., *J. Med. Chem.,* 32: 2503–7 (1989).

The glycosylated polyamine compounds of Formula I can be provided in a pharmaceutically acceptable carrier. The pharmaceutical composition includes one or more of the glycosylated polyamines in an effective amount for the treatment of a condition. The term "effective amount" refers to an amount sufficient to effect beneficial or desired pharmacological or clinical results. The amount can be determined based on such factors as the type and severity of symptoms being treated, the weight and/or age of the subject, the previous medical history of the subject, and the selected route for administration of the agent. The determination of appropriate "effective amounts" is within the ordinary skill of the art.

The term "administration" is intended to include routes of administration which allow the agent (e.g. anticancer agent) to perform its intended finction, e.g., reducing the tumor mass or growth. Examples of routes of administration which can be used include injection (subcutaneous, intravenous, parenterally, intraperitoneally, etc.), oral, inhalation, trandsdermal, and rectal. Depending on the route of administration, the agent can be coated with or in a material to protect it from the natural conditions which may detrimentally effect its ability to perform its intended function. The administration of the agent is done at dosages and for periods of time effective to significantly reduce or eliminate tumor mass or growth. Dosage regimes may be adjusted for purposes of improving the therapeutic response of the agent. For example, several divided doses may be administered daily or the dose may be proportionally reduced as indicated by the exigencies of the therapeutic situation.

The compounds, or their pharmaceutically acceptable salts, prodrugs and derivatives and combinations thereof described herein can be provided and administered in a pharmaceutically acceptable carrier. The phrase "pharmaceutically acceptable carrier" is intended to include substances capable of being co-administered with the agent and which allow the agent to perform its intended function, e.g. reducing tumor mass or growth. Examples of such carriers include solvents, dispersion media, delay agents and the like. The use of such media and agents for pharmaceutically active substances is well known in the art. Any conventional media and agent compatible with the compound can be used with this invention. The compound compositions further can be co-administered with other agents such as art-recognized protein enhancing agents, differentiating agents, and/or adjuvants.

Thus, a glycosylated polyamine compound or a composition comprising the compound, can be administered in an effective amount to treat a condition, such as cancer, or to obtain a desired clinical result, such as remission or cure of such cancerous condition. The compounds and compositions are administered in vitro, in vivo, or ex vivo, depending on the particular circumstances if the treatment, including the disease, dosage, patient's age, and health among other factors.

"In vitro" use of a material is defined as a use of a material or compound outside a living human, mammal, or vertebrate, where neither the material nor compound is intended for reintroduction into a living human, mammal, or vertebrate. An example of an in vitro use would be the analysis of components of a blood sample using laboratory equipment. "In vivo" use of a material is defined as introduction of the material into a living human, mammal, or vertebrate.

"Ex vivo" use of a compound is defined as using a compound for treatment of a biological material outside a living human, mammal, or vertebrate, where that treated biological material is intended for use inside a living human, mammal, or vertebrate. For example, removal of blood from a human, and introduction of a compound into that blood, is defined as an ex vivo use of that compound if the blood is intended for reintroduction into that human or another human. Reintroduction of the human blood into that human or another human would be in vivo use of the blood, as opposed to the ex vivo use of the compound. If the compound is still present in the blood when it is reintroduced into the human, then the compound, in addition to its ex vivo use, is also introduced in vivo.

The glycosylated polyamine compounds described herein and their salts, prodrugs may be used directly by themselves or may be incorporated into a medicament preparation for treating an ailment such as cancer. Thus, depending on the intended mode, the compositions may be in the solid, semi-solid or liquid dosage form, such as, for example, injectables, tablets, suppositories, pills, time-release capsules, powders, liquids, suspensions, or the like, including in unit dosage formulations. The compositions, while including an effective amount of a glycosylated polyamine compound of the present invention, or the pharmaceutically acceptable salt thereof, in addition, may include any conventional pharmaceutical excipients and other medicinal or pharmaceutical drugs or agents, carriers, adjuvants, diluents, etc., as customary in the pharmaceutical sciences.

For solid compositions such excipients include pharmaceutical grades of mannitol, lactose, starch, magnesium stearate, sodium saccharin, talcum, cellulose, glucose, sucrose, magnesium carbonate, and the like may be used. The glycosylated polyamines as described above, may be also formulated as suppositories using, for example, polyalkylene glycols, for example, propylene glycol, as the carrier.

Liquid, particularly injectable compositions can, for example, be prepared by dissolving, dispersing, a glycosylated polyamine of the invention in a pharmaceutical solution such as, for example, water, saline, aqueous dextrose, glycerol, ethanol, and the like, to thereby form the injectable solution or suspension.

If desired, the pharmaceutical composition to be administered may also contain minor amounts of nontoxic auxiliary substances such as wetting or emulsifying agents, pH buffering agents, and the other substances such as for example, sodium acetate, triethanolamine oleate, etc.

Parenteral injectable administration is generally used for subcutaneous, intramuscular or intravenous injections and infusions. Injectables can be prepared in conventional forms, either as liquid solutions or suspensions or solid forms suitable for dissolving in liquid prior to injection.

The above preparations can be made into slow-release or sustained-released systems, which provide a constant level of dosage. Such sustained release preparations are well-known in the art. See, for example, U.S. Pat. No. 3,710,795. Actual methods of preparing such dosage forms are known, or will be apparent to those skilled in this art, and are in detail described in Remington's Pharmaceutical Sciences, Mack Publishing Company, Easton, Pa., 17th Edition, 1985.

Any of the above pharmaceutical compositions may contain 0.1–99% of the glycosylated polyamine. An effective dosage may be in the range of 0.001 to 5000 mg/kg/day, preferably 0.01 to 1000 mg/kg/day, more preferably 0.1 to 100 mg/kg/day. Generally, the upper limit for the drug dose determination is its efficacy balanced with its possible toxicity.

The pharmaceutical compositions of this invention can contain one or more compounds of the Formula I described above and, if desired, can be employed in combination with other therapeutic agents including conventional anti-tumor agents known in the art. Suitable examples of such conventional anti-tumor agents which can be used include adriamycin, cisplatin, colchicine, CCNU, BCNU, Actinomycin D, 5-fluorouracil, thiotepa, cytosinearabinoside, cyclophosphamide, mitomycin C, and the like.

In addition to their anti-cancer activities, the compounds of the invention can be used in a variety of other methods involving modulation of estrogen receptor -activity, for example in the general management of post-menopausal women's health. In addition to the treatment of breast cancer as described above, compounds of the invention also can be used for preventing breast cancer, or delaying the onset of breast cancer, in subjects at risk for breast cancer (e.g., subject with a family history of breast cancer or subjects carrying a breast cancer marker gene such as BRCA1 or BRCA2). Accordingly, the invention provides a method for treating, preventing or delaying onset of breast cancer in a subject having or at risk for breast cancer, comprising administering a compound of the invention to the subject.

In another embodiment, the compounds of the invention can be used to treat, prevent or delay onset of osteoporosis. The invention provides a method for treating, preventing or delaying onset of osteoporosis in a subject having or at risk for osteoporosis, comprising administering a compound of the invention to the subject.

In yet another embodiment, the compounds of the invention can be used to modulate reduce the risk of cardiovascular disease, for example by lowering cholesterol levels. The invention provides a method of reducing risk of cardiovascular disease in a subject, comprising administering a compound of the invention to the subject.

In yet another embodiment, the compounds of the invention can be used to modulate ovulation, for example to induce ovulation (e.g., for purposes of fertility treatment) or to inhibit ovulation (e.g., for purposes of contraception). The invention provides a method of modulating ovulation in a subject comprising administering a compound of the invention to the subject.

Compounds of the invention having ER-antagonist effects in uterine tissue can be used to treat, prevent or delay onset of uterine disorders, including endometriosis, dysfunctional uterine bleeding and fibroids. The invention provides a method for treating, preventing or delaying onset of a uterine disorder, comprising administering a compound of the invention to the subject.

The compounds of the present invention may be susceptible to hydrolysis because they possess C—N glycosidic linkages and this hydrolysis might reduce their therapeutic efficacy against certain cancer cell lines. Accordingly, one aspect of this invention provides compounds of Formula I having C—C glycosidic linkage, instead of a C—N glycosidic linkage. An example of a hexosyldiethylenetriamine having a C—C glycosidic linkage can be shown as below:

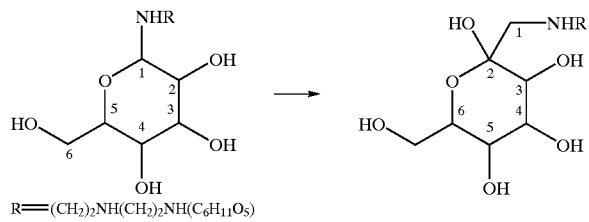

One method of forming such C—C linkage is described in Ledl, F. and Schleicher, E., *Angew. Chem. Int. Ed. Engl.*, 29: 565 (1990).

Metal Complexes of Glycosylated Polyamines

Metal complexes of glycosylated polyamines may be formed with metal compounds such as metals or metal salts. The metal complexes can be rapidly prepared and characterized for the stereospecificity of their glycosyl linkages. Such stereochemistry-differentiating systems are useful for elucidating total synthesis of complex molecules such as natural products and also for preparing and identifying biologically more active compounds wherein the activity may reside in a particular stereoisomer.

Thus, a compound of the formula $R_1$—Z—$R_2$ (Formula I), can be complexed to a metal compound Y, to produce a metal-polyamine-glycosyl complex having the following structure (Formula II):

$$[R_1—Z—R_2]\cdot Y \qquad \text{(Formula II)}$$

wherein Formula I is as described above and Y is a metal compound. The metal compound Y is a metal such as zinc, or a metal salt such as zinc chloride, zinc acetate, zinc triflate, sodium chloride magnesium chloride, copper chloride, cobalt chloride, nickel chloride, or calcium carbonate. In addition, the metal salts can be also those of organic origin such as sulfonate triflate or tosylate. Thus, a glycosylated polyamine-metal complex such as N,N'-diglucosyl diethylenetriamine can be complexed to a metal compound such as zinc chloride.

One general structure of a dihexosyldiethylenetriamine-zinc chloride complex is shown below:

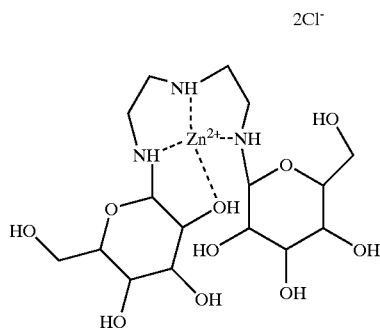

In one preferred example of a dihexosyldiethylenetriamine-zinc chloride complex, the hexose is a glucose. In some cases, the hexose residue possesses a group other than a hydrogen in axial conformation at its C2 position, whereas in other cases, the hexose residue possesses a group other than hydrogen in equatorial conformation at its C2 position. Mannose, for example, possesses a hydroxyl group in axial conformation at its C2 position, whereas glucose, for example, possesses a hydroxyl group in equatorial conformation at its C2 position.

Some additional examples of groups that may be present at the C2 position include groups such as alkoxy, halo, lower alkyl, amino, N-acetyl, N-alkyl, N-hydroxy, N-alkoxy, aminothiol, amino alcohol, spermine, or nitro group, and optionally a hydrogen in the axial conformation, provided that at least one of the residues of $R_1$ and $R_2$ has a group that has an acidic hydrogen at the C2 position of the saccharide residue that forms glycosidic bond with the polyamine to form a hydrogen bond with the metal. For example, if $R_1$ is a glucose, $R_2$ can be a glucose that has its C2 hydroxyl substituted by a nitro or a halo group. Additional examples of such acidic hydrogen containing groups include hydroxyl, thio, acyl, carboxyl, and hydroxyamino.

Preparation of Metal Complexes of Glycosylated Polyamines

One method for preparing the metal complexes of glycosylated polyamines comprises mixing a glycosylated polyamine, for example, a compound of the formula [$R_1$—Z—$R_2$], Formula I, as described hereinabove, with an equimolar amount of a metal compound Y and an inorganic salt prepared from a weak base-strong acid system, such as ammonium hydroxide, in an organic solvent, such as methanol, to form a metal complex, which optionally can be further purified.

The method presented herein is a rapid method to prepare metal complexes, wherein the metal complex is often formed in a relatively short time, for example, within a few minutes of the mixing of the glycosylated polyamine and the metal compound as described above. Moreover, the metal complex formed by this method gives rise to a suitable parent ion when analyzed using a mass spectrometer. This parent ion can be collisionally activated to give rise to a product ion that is characteristic of a specific configuration of the glycoside. Thus, the mass spectrum reveals whether the glycosidic linkage is an alpha or a beta linkage.

An exemplary general reaction scheme to prepare a dihexosyldiethylenetriamine zinc chloride complex is shown below:

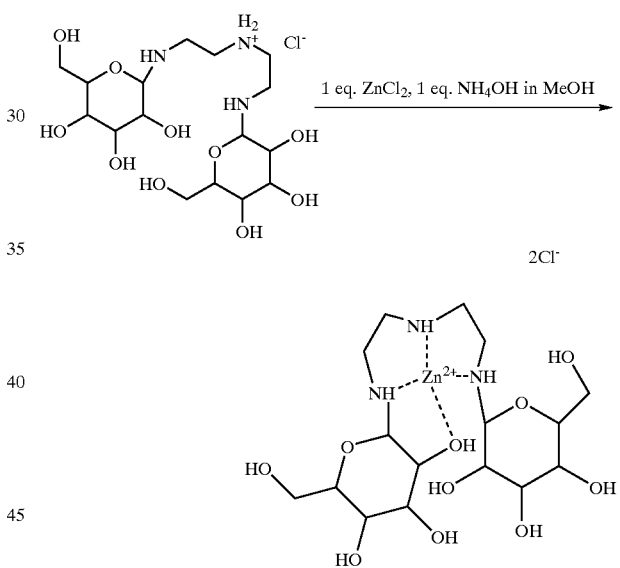

Analytical Methods Using Metal Complexes of Glycosylated Polyamines

It is well known that saccharides exist in many stereoisomeric forms. One particular type of such stereoisomerism is the presence of an alpha or beta linkage at the anomeric carbon, giving rise to alpha and beta anomers. A rapid analytical method to distinguish stereoisomers of a disaccharide is provided.

In one aspect, the glycosylated polyamine of Formula I as described above is cationized using a metal compound Y to form a metal-polyamine-N-glycoside complex (Formula II, supra), wherein, at least one of $R_1$ and $R_2$ is a disaccharide. Some examples of such metal-polyamine-glycosyl complexes include zinc(diethylenetriamine-diglucosyl)$_2$Cl$_2$ or nickel(1,3-diaminopropane-diglucosyl)$_3$Cl$_2$. The metal-polyamine-N-glycoside complex is then ionized and the ions are detected using one or more mass spectrometers.

The metal-N-glycoside complex can be ionized by using a variety of ionization techniques. Some examples of such ionization techniques include, electron impact, chemical ionization, field desorption, electrospray or fast atom bombardment ionizations and matrix assisted laser desorption ionization. The ion detection is accomplished for example, by using two or more mass spectrometers arranged in tandem, in space and time, for example as triple quad instruments or those employing ion trap or ion cyclotron resonance technology. The mass spectrometers can be of different types, and include quadruple mass spectrometers. Further, the mass spectrometers can be operated manually, or automated through a computer program.

Methods for Detecting Axial or Equatorial Conformation

Axial or equatorial conformations are present in many types of structures, including saccharides. The detection of such conformations are of great interest in carbohydrate chemistry because knowledge of the conformation helps in elucidating or establishing total synthesis and also in correlating stereochemistry with biological activity.

The presence of an axial or equatorial conformation of a group other than hydrogen at, for example, the C2 position of a saccharide can be detected by: a) reacting an aliphatic polyamine and the saccharide in the presence of a precipitating agent; b) observing for a precipitate in the reaction mixture; and c) noting the presence of an axial conformation of the group at the C2 position if no precipitate is observed within a certain time after the reaction according to step a).

The aliphatic polyamine and the saccharide are reacted at a certain ratio, for example, at about a 1:2 molar ratio. The precipitating agent is present in less than or equal to 1 molar concentration. In some cases, the precipitate can be observed within a few minutes, whereas in other cases the precipitate is formed within a few hours, provided that the saccharide has a group other than a hydrogen in equatorial conformation at the C2 position.

The group whose conformation at C2 is being determined can be an alkoxy, halo, lower alkyl, amino, N-acetyl, N-alkyl, N-hydroxy, N-alkoxy, aminothiol, amino alcohol, spermine, or nitro group. The saccharide may be, for example, a monosaccharide comprising a pentose, hexose, or an oligosaccharide residue. The precipitating agent can be any acidic salt that provides a halo counterion, for example, HCl, HBr, HI. Preferably, the counterion is a chloride ion. The aliphatic polyamine includes polyamines such as triethylene tetramine, diethylene triamine, ethylene diamine, and diaminopropane.

The saccharide of interest can be a monosaccharide having 4 to 7 carbon atoms or an oligosaccharide consisting of any two or more monosaccharides. Some examples of monosaccharides include glucose, galactose, fucose, or allose. The oligosaccharide may, as described supra, consist of any two or more monosaccharides joined through one or more glycosidic linkages.

When each of the saccharide residues, $R_1$ and $R_2$ is a monosaccharide residue, it must be the same monosaccharide. When each of the saccharide residues, $R_1$ and $R_2$, is an oligosaccharide residue, the saccharide unit that forms the N-glycosyl bond with the amine of the polyamine linker must be the same for each oligosaccharide residue. Alternatively, one of $R_1$ or $R_2$ can be a monosaccharyl and the other can be an oligosaccharyl, provided that, in case of the oligosaccharide, the saccharide unit that forms the N-glycosyl bond with the amine of the polyamine linker must be the same as the monosaccharide.

For example, if $R_1$ is an oligosaccharide that consists of glucose-mannose-allose residues and it is the allose that is involved in glycosidic linkage with the amino group of the polyamine linker, then $R_2$ must be an allose residue or the glycosidic-bond forming saccharide unit of an oligosaccharide. Additionally, the group whose conformation at the C2 position is being determined should preferably be the same on each saccharide residue that is involved in glycosidic linkage with the amino group of the polyamine linker.

Optionally, the method can be automated either to prepare the chloride salt of the glycosylated polyamine or to observe the presence or absence of the precipitate. A variety of methods can be used to observe the chloride precipitate, and include colorimetric, and spectrophotometric methods. The observation of the precipitate, either manually or through automation, is within the capability of one of ordinary skill in the art.

Some specific examples where an equatorial conformation at the C2 position of a saccharide were determined include glucose, galactose, allose or fucose. One specific example where an axial conformation at the C2 position was determined is in the case of mannose. Additional examples can include oligosaccharides wherein the sugar moiety forming the N-glycosidic linkage with the polyamine is a hexose, such as, glucose, galactose, allose, fucose, or mannose.

The following specific examples are presented to illustrate the preparative methods for representative compounds useful in the method of this invention, to provide relevant data regarding useful compounds, and to illustrate the manner in which the activity of the compounds is determined, and are not to be construed as limiting the scope of the invention.

EXAMPLES

General Procedures

In the Examples, $^{1}$H-NMR and $^{13}$C-NMR spectra were recorded on a 500 MHz instrument in $D_2O$. MS analyses were carried out in the positive ion mode using electrospray ionization on an ion trap instrument as described in Gaucher, S. P. and Leary, J. A., *Anal. Chem.*, 70: 3009 (1998). D-Glucose, diethylenetriamine and 1M HCl in ether were purchased from Aldrich (Milwaukee, Wis.). D-Allose was purchased from ICN Biomedicals, Inc. (Aurora, Ohio). D-Galactose and L-fucose were purchased from Sigma (St. Louis, Mo.). Ammonium hydroxide, zinc chloride, cobalt chloride, and nickel chloride were purchased from Fisher (Pittsburgh, Pa.). Copper chloride was purchased from Mallinckrodt (Phillipsburg, N.J.). All reagents were used as received.

Example 1

Preparation of 1,3-N,N-di-β-D-glucopyranosyl-diethylenetriamine (1)

Diethylenetriamine (1.56 mL, 14.4 mmol) was dissolved in methanol (15 L) and cooled to 0° C. Hydrochloric acid (1 M solution in ether, 14.4 mL, 14.4 mmol) was added dropwise with stirring. The flask was warmed to room temperature and methanol (50 mL) was added to redissolve the white precipitate which had appeared. Glucose (5.19 g, 28.8 mmol) which had been dissolved in 6 mL of hot water was added to the reaction flask followed by 6 mL more methanol. The resulting solution remained clear for 20 min after which time a white precipitate appeared. The reaction mixture was allowed to stir for 1.25 hr, and the precipitate was collected and dried under vacuum to give 5.38 g of (1).

Recrystallization of (1) was achieved by dissolving 661 mg of the precipitate in 5 mL of water in a large test tube. A 45 mL portion of 50:50 ethanol:methanol was carefully added to the tube and allowed to slowly infuse into the water layer with gentle swirling as necessary. Once crystals had begun to form, the solution was left at room temperature for 30 more minutes and then kept at 0° C. overnight before filtering to obtain 413 mg of white crystalline product (greater than 90% overall yield).

$^1$H-NMR: δ2.40–3.10 (10H, m), δ3.15–3.35 (6H, m), δ3.52 (2H, dd, J=5.5, 12.0 Hz), δ3.72 (2H, dd, J=1.5, 11.0 Hz), δ3.86 (2H, d, J=8.5 Hz); $^{13}$C-NMR: δ41.25, 47.39(—CH2—CH2—), δ60.78 (C6/C6'), δ69.75, 72.86, 76.49, 76.53 (C2–C5/C2'–C5'), δ89.52 (C1/C1'); MS: [M+H]$^+$ m/z 428. Anal. Calc. for $C_{16}H_{34}ClN_3O_{10}$: C, 41.42; H, 7.39; N, 9.06. Found: C, 41.12; H, 7.63; N, 8.90.

Example 2

Preparation of 1,3-N,N-di-β-D-galactosylpyranosyl-diethylenetriamine (2)

Diethylenetriamine (0.52 mL, 4.8 mmol) was dissolved in methanol (15 mL). Hydrochloric acid (1 M in ether, 4.8 mL, 4.8 mmol) was added dropwise with stirring at room temperature. Galactose (1.73 g, 9.6 mmol) which had been dissolved in 2 mL hot water was added to the reaction flask along with 10 mL more methanol. The resulting solution remained clear for 15 min after which time a white precipitate appeared. The reaction mixture was allowed to stir 1 hr and then kept at 4° C. overnight. The crude product was collected and dried 2.5 hr under vacuum to give 1.90 g. A 600 mg portion of crude material was recrystallized as for (1) using 2 mL water and 10 mL ethanol/methanol to yield 336 mg product (48% overall yield).

$^1$H-NMR: δ2.99–3.10 (7H, m), δ3.34 (2H, dd, J=8.5, 9.5 Hz), δ3.50–3.64 (9H, m), δ3.81 (2H, dd, J=1.0, 3.5 Hz), δ3.86 (2H, d, J=9.0 Hz); $^{13}$C-NMR: δ41.35, 47.52 (—CH2—CH2—), δ61.18 (C6/C6'), δ68.90, 70.59, 73.43, 75.70 (C2–C5/C2'–C5'), δ90.04 (C1/C1'); MS: [M+H]$^+$ m/z 428. Anal. Calc. for $C_{16}H_{34}ClN_3O_{10}$: C, 41.42; H, 7.39; N, 9.06. Found: C, 41.05; H, 7.69; N, 8.82.

Example 3

Preparation of 1,3-N,N-di-β-D-allopyranosyl-diethylenetriamine (3)

The reaction was carried out as for (2) using 0.31 mL (2.9 mmol) of diethylenetriamine, 4.8 mL (2.8 mmol) 1 M HCl in ether, and 1.0 g (5.6 mmol) of allose instead of galactose. Crude yield 1.2 g. A 241 mg portion of crude material was recrystallized as for (1) using 0.75 mL water and 12 mL ethanol/methanol to yield 179 mg product (67% overall yield).

$^1$H-NMR: δ2.94–3.06 (8H, m), δ3.29 (2H, dd, J=2.8, 9.6 Hz), δ3.45 (2H, dd, J=2.5, 9.5 Hz), δ3.5–3.6 (4H, m), δ3.74 (2H, dd, J=1.5, 11.5 Hz), δ4.02 (2H, dd), δ4.12 (2H, d, J=9.5 Hz); $^{13}$C-NMR: δ41.35, 47.47 (—CH2—CH2—), δ61.26 (C6/C6'), δ67.00, 70.08, 70.90, 73.71 (C2–C5/C2'–C5'), δ86.22 (C1/C1'); MS: [M+H]$^+$ m/z 428. Anal. Calc. for $C_{16}H_{34}ClN_3O_{10}$: C, 41.42; H, 7.39; N, 9.06. Found: C, 41.59; H, 7.64; N, 8.96.

Example 4

Preparation of 1,3-N,N-di-β-D-fucopyranosyl-diethylenetriamine (4)

The reaction was carried out as for (2) using fucose (1.58 g, 9.6 nmmol) instead of galactose. The crude product was dried 6 hr under vacuum to yield 1.74 g. A 425 mg portion of material was recrystallized as for (1) using 1 mL water and ~12 mL ethanol/methanol to yield 213 mg product (42% overall yield).

$^1$H-NMR: δ1.05 (6H, d, J=6 Hz), δ2.7–3.0 (8H, m), δ3.2–3.3 (2H, m), δ3.47 (2H, dd, J=3.5, 10.0 Hz), δ3.6–3.7 (4H, m), δ3.78 (2H, d, J=9.0 Hz); $^{13}$C-NMR: δ15.74 (C6/C6'), δ41.18, 47.35 (—CH2—CH2—), δ70.34, 71.37, 71.57, 73.55 (C2–C5/C2'–C5'), δ89.76 (C1/C1'); MS: M+H m/z 428. Anal. Calc. for $C_{16}H_{34}ClN_3O_{10}$: C, 44.50; H, 7.88; N, 9.73. Found: C, 44.42; H, 8.10; N, 9.54.

The methods described in the above Examples is a general method for preparing compounds of the general formula $R_1$—Z—$R_2$ as described supra in the detailed description. This general method is a convenient one-pot synthesis in which the crude product precipitated from solution in high yield (80–90%). In general, yields can be improved by allowing the reaction to stir for 1 hr after initial observation of the precipitate and then cooling to 4° C. before filtration.

$^{13}$C-NMR spectra indicate that all of these compounds have an axis of symmetry because the eight carbon environments present in the spectra of (1) through (4) is half of the total number of carbon atoms in the molecule. In the $^1$H-NMR spectra of (1) through (4) the anomeric hydrogen is a doublet with a coupling constant of 8.5 to 9.5 Hz. Such coupling constants are in the range for those resulting from an axial-axial configuration of H1 and H2 and therefore, for these sugars, a β N-glycosidic linkage. Silverstein, et al., *Spectrometric Identification of Organic Compounds*, 5th ed.; John Wiley: New York, p221 (1991).

The NMR spectra of (1) through (4) are complicated by the fact that the only solvent these compounds are very soluble in is $H_2O$ which leads to partial hydrolysis of the N-glycoside bonds within 5 min. Solubility in other polar solvents such as DMSO is negligible. To maximize sample concentration and minimize hydrolysis time, the spectra were obtained in $D_2O$ using very concentrated samples (0.6 to 0.7 M) on a high field instrument (500 MHz). The identity and connectivity information from the $^{13}$C- and $^1$H-NMR data is consistent with an X-ray crystal structure of compound (1). The reaction could be stereoselective with preference for the form ation of the 0 isomer.

Example 5

Preparation of Glycosylated Polyamine Metal Complexes

Metal complexes of glycosylated polyamine compounds can be prepared by mixing equimolar amounts of the glycosyl polyamine ligand compound and a metal such as zinc chloride and ammonia in methanol. The reaction mixture is vortexed for about a minute and can be prepared for mass spectral analysis directly, without isolation and purification.

Sample Preparation. Diglycosyl-diethylenetriamine "templates" were prepared as described elsewhere. Briefly, one equivalent each of dien and 1.0 M HCl in ether were allowed to react in methanol to form a dien-HCl salt. Two equivalents of either glucose or galactose were added and the product, which precipitated from solution, was recrystallized from ethanol/water.

Figure 2:
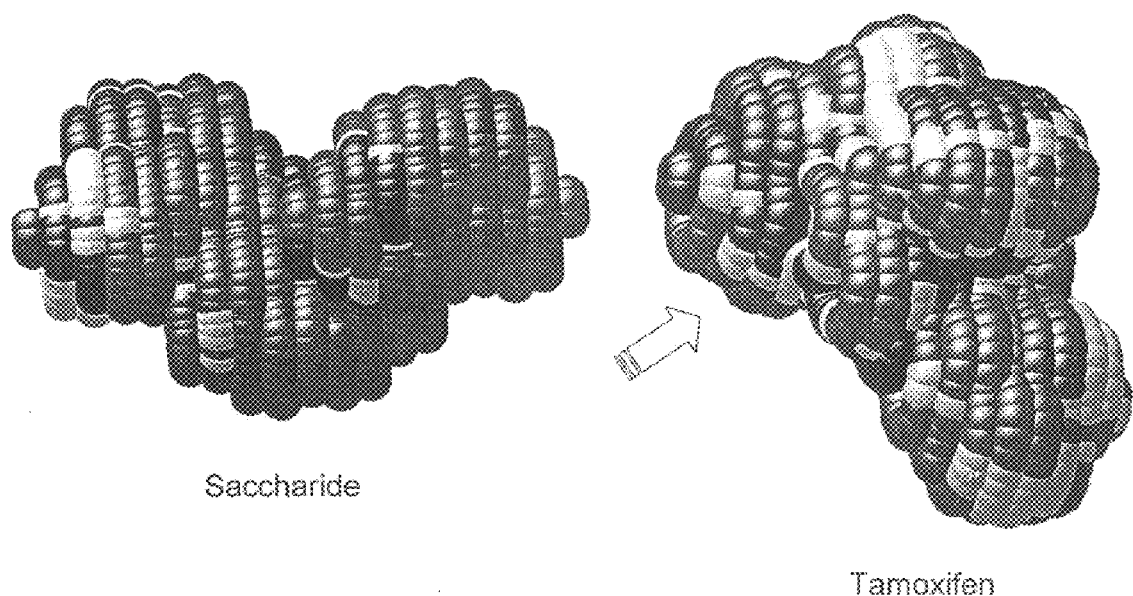
FIG. 2 is a schematic diagram of the solvent accessible surface surrounding diglucosyl diethylenetriamine (SPG-20) (left) in comparison to tamoxifen (right).

Samples were prepared by first allowing 1–2 mg of "template" to partially hydrolyze in 10 μL $H_2O$ for 1 hr to form a mixture in solution of mono and di N-glycosides (see FIG. 2). A 200 μL portion of methanol was added along with approximately 2–4 equivalents of metal chloride and 1 μL concentrated $NH_4OH$ (except in the case of $CoCl_2$ samples where no base was added). Solutions were diluted in 100% methanol for analysis with final concentrations of 50–100 pmol/μl in "template."diluted in 100% methanol for analysis with final concentrations of 50–100 pmol/□L in "template."

Mass Spectrometry. Mass spectral analyses were performed on a quadrupole ion trap mass analyzer (Finnigan LCQ, Finnigan MAT, San Jose, Calif.) fitted with the electrospray ionization (ESI) source. Samples were infused into the instrument at a rate of 2 µL/min. The needle was held at a potential of 4.6–5.0 V. Ions were trapped by applying an rf-only potential to the ring electrode, and the automatic gain control was set to $5 \times 10^7$ counts and $3 \times 10^7$ counts for MS and $MS^n$ respectively to regulate the number of ions present in the trap.

Ligands such as (1) provide simple and efficient routes to various metal N-glycoside complexes which are of interest in the solid state. The metal complexes are rapidly formed and further facilitate rapid characterization of the stereospecificity of saccharides by giving rise to a prominent and characteristic parent ion in a mass spectrum. For example, the mass spectrum of the products from the above method consists predominantly of singly and doubly charged metal N-glycoside complexes. On the other hand, a previously known procedure yields only a moderate to low abundance of these ions of interest, along with many other species which are presumably side reactions and unreacted starting material. In the previously known procedure, the metal-polyamine salt such as $Zn(NH_2(CH_2)_2NH(CH_2)_2NH_2)_3Cl_2$ is heated with a hexose at 50° C. for 20 minutes to form the glycosylated-polyamine-metal complex.

Example 6
Method for Detecting Equatorial or Axial Substitution of a Saccharide

The experiment described in Example 1 above was repeated but this time using D-mannose and D-altrose instead of D-glucose. The diglycosyl product could not be precipitated even though its formation could be established through mass spectrometry.

The X-ray crystal structure obtained for (1) gives some insight as to why crystalline products were easily obtained for (1–4) while the corresponding reaction with mannose did not yield a precipitate, even though mass spectrometric analysis indicated that the desired dimannosyltriamine had been formed in solution. From X-ray crystallographic data, the chloride ion imparts some rigidity to the structure. There are hydrogen bonds from the central nitrogen and from the hydroxyl groups on C2/C2' to the chloride ion. The latter observation is relevant because glucose, galactose, allose, and fucose all possess an equatorial C2 hydroxyl group while mannose has an axial C2 hydroxyl.

Examination of the Ortep diagram reveals that in order for the H-bonding to occur between chloride and the axial hydroxyl groups on C2/C'2 of the mannose moiety, significant structural contortion would be necessary which might then preclude crystallization. This hypothesis was further confirmed when the reaction was repeated, this time using altrose, which also possesses an axial C2 group. As expected no solid product was formed under these conditions, although the major product detected by mass spectrometric analysis was the protonated diglycosylamine complex (m/z 428).

No precipitate was observed after several hours when the synthesis of (1) was repeated, omitting the addition of HCl. When one equivalent of HCl in ether was added to the reaction mixture, however, (1) precipitated from solution. This result supports the conclusion that under these conditions the chloride ion is playing an important role in the crystallization process. The fact that attempts to induce crystallization of (1) with bulkier counterions such as $HSO_4-$, $NO_3-$, and $CH_3COO-$ were unsuccessful suggests that these counterions are not suited for the space provided by the two monosaccharide and "bridging" diethylenetriamino moieties.

Example 7
Biological Experiments to Show Antitumor Activity

The present compounds are tested in vitro for their antitumor activity against a variety of tumor cell lines well-known in the art. These tumor cell lines are known to correlate in vitro and in vivo activity and thus represent good screening system to predict in vivo activity. The methodology to evaluate antitumor activity is well-known in the art. See for example, U.S. Pat. Nos. 5,789,418; 5,661,155; and 5,206,249, and Li, L. H. et al., Cancer Res., 39: 4816–4822 (1979)). Efficacy in such models is indicative of utility in the treatment of tumors in human patients and evidences important therapeutic utility in the treatment of cancer.

A. In vitro methodology

Cytotoxicity may be measured using a standard methodology for adherent cell lines such as the microculture tetrazolium assay (MTT). Details of this assay have been published (Alley, M C et al, Cancer Research 48:589–601, 1988). Exponentially growing cultures of tumor cells such as the HT-29 colon carcinoma or LX-1 lung tumor can be used to make microtiter plate cultures. Cells can be seeded at 5000–20,000 cells per well in 96-well plates (in 150 µl of media), and grown overnight at 37° C. Test compounds are added, in 10-fold dilutions varying from $10^{-4}$ M to $10^{-10}$ M. Cells are then incubated for 48–72 hours. To determine the number of viable cells in each well, the MTT dye is added (50 µl of 3 mg/ml solution of 3-(4,5-dimethylthiazol-2-yl)-2,5-diphenyltetrazolium bromide in saline). This mixture is incubated at 37° C. for 5 hours, and then 50 µl of 25% SDS, pH 2 is added to each well. After an overnight incubation, the absorbance of each well at 550 mn is read using an ELISA reader. The values for the mean+/–SD of data from quadruplicate wells are calculated, using standard formula as for the %T/C (%viable cells treated/control). Additional methods as described by Inhibition of the growth of tumor cells was determined as described by Patil, S. D., et al J. Med. Chem., 32, 1284 (1989) may be used as well.

The concentration of test compound which gives a T/C of 50% growth inhibition is designated as the $IC_{50}$.

Cells and Medium

Cell cultures representing various cancerous conditions were tested. Representative examples include: CCRF-CEM and MOLT-4 for leukemia; A549/ATCC, HOP-92, NCI-H522 for non-small cell lung cancer; DMS 114 and SHP-77 for small cell lung cancer; COLO 205, HCT-15, HT29, SW-620 for colon cancer; SF-268, SF-295, SNB-78, XF498 for CNS cancer; M14, SK-MEL-28, UACC-62 for melanoma; IGROV1, OVCAR-8, SK-OV-3 for ovarian cancer; A498, RXF-321, UO-31 for renal cancer; PC-3, DU-145 for prostate cancer; MCF7, MDA-MB-435, MAXF 401, SK-BR-3 for breast cancer. The complete list of cell lines tested are given in the following table.

Typically, the cells are grown in RPMI 1640 medium supplemented with 10 nM calcium leucovorin instead of folic acid as the folate source, 10% dialyzed fetal calf serum, penicillin and streptomycin. Additional ingredients may be added depending on the particular needs of the cells being cultured. For example, in the case of colon carcinoma cell cultures, lung carcinoma cell cultures, and breast carcinoma cell lines, the above medium may be further supplemented with sodium pyruvate, (110 g/ml).

Cytotoxicity Assay

Cells are seeded into 96-well plates using a pipeting mechanism such as Perkin-Elmer Pro/pette. Cells are seeded depending on the characteristics of their growth, but typically, may range from at 8,000 cells per well to at 12,500 cells per well, all in, for example, a 150 mL of medium. Prior to the addition of the glycosylated polyamine compounds of the present invention, cultures are incubated for 24 hrs at 37° C. The compounds are added at 2× concentration in 150 mL of medium and each concentration is assayed in triplicate. If DMSO or ethanol are used to solubilize compounds, appropriate controls are run if the concentration exceeded 0.01%. Cultures are incubated for 72 hours (96 hours in some cases) in a 37° C. humidified incubator at 5% $CO_2$. Inhibition of cell growth may be measured using the MTT dye reduction assay as described above.

The in vitro tumor cell lines include, but not limited to, one or more of the following cell lines representing various forms of cancers.

| Cell Line | Cancer Model |
|---|---|
| CCRF-CEM | Leukemia |
| HL-60(TB) | Leukemia |
| K-562 | Leukemia |
| MOLT-4 | Leukemia |
| RPMI-8226 | Leukemia |
| SR | Leukemia |
| A549/ATCC | Non-Small Cell Lung Cancer |
| EKVX | Non-Small Cell Lung Cancer |
| HOP-18 | Non-Small Cell Lung Cancer |
| HOP-19 | Non-Small Cell Lung Cancer |
| HOP-62 | Non-Small Cell Lung Cancer |
| HOP-92 | Non-Small Cell Lung Cancer |
| NCI-H226 | Non-Small Cell Lung Cancer |
| NCI-H23 | Non-Small Cell Lung Cancer |
| NCI-H322M | Non-Small Cell Lung Cancer |
| NCI-H460 | Non-Small Cell Lung Cancer |
| NCI-H522 | Non-Small Cell Lung Cancer |
| LXFL 529 | Non-Small Cell Lung Cancer |
| DMS 114 | Small Cell Lung Cancer |
| DMS 273 | Small Cell Lung Cancer |
| SHP-77 | Small Cell Lung Cancer |
| COLO 205 | Colon Cancer |
| DLD-1 | Colon Cancer |
| HCC-2998 | Colon Cancer |
| HCT-116 | Colon Cancer |
| HCT-15 | Colon Cancer |
| HT29 | Colon Cancer |
| KM12 | Colon Cancer |
| KM20L2 | Colon Cancer |
| SW-620 | Colon Cancer |
| SF-268 | CNS Cancer |
| SF-295 | CNS Cancer |
| SF-539 | CNS Cancer |
| SNB-19 | CNS Cancer |
| SNB-75 | CNS Cancer |
| SNB-78 | CNS Cancer |
| TE671 | CNS Cancer |
| U251 | CNS Cancer |
| XF 498 | CNS Cancer |
| LOX IMVI | Melanoma |
| MALME-3M | Melanoma |
| M14 | Melanoma |
| RPMI-7951 | Melanoma |
| M19-MEL | Melanoma |
| SK-MEL-2 | Melanoma |
| SK-MEL-28 | Melanoma |
| SK-MEL-5 | Melanoma |
| UACC-257 | Melanoma |
| UACC-62 | Melanoma |
| IGROV1 | Ovarian Cancer |
| OVCAR-3 | Ovarian Cancer |
| OVCAR-4 | Ovarian Cancer |
| OVCAR-5 | Ovarian Cancer |
| OVCAR-8 | Ovarian Cancer |
| SK-OV-3 | Ovarian Cancer |
| 786-0 | Renal Cancer |
| A498 | Renal Cancer |
| ACHN | Renal Cancer |
| CAKI-1 | Renal Cancer |
| RXF 393 | Renal Cancer |

-continued

| Cell Line | Cancer Model |
|---|---|
| RXF-631 | Renal Cancer |
| SN12C | Renal Cancer |
| SN12K1 | Renal Cancer |
| TK-10 | Renal Cancer |
| UO-31 | Renal Cancer |
| P388 | Leukemia |
| P388/ADR | Leukemia |
| PC-3 | Prostate Cancer |
| DU-145 | Prostate Cancer |
| MCF7 | Breast Cancer |
| NCI/ADR-RES | Breast Cancer |
| MDA-MB-231/ATCC | Breast Cancer |
| HS 578T | Breast Cancer |
| MDA-MB-435 | Breast Cancer |
| MDA-N | Breast Cancer |
| BT-549 | Breast Cancer |
| T-47D | Breast Cancer |
| MAXF 401 | Breast Cancer |
| MDA-MB-468 | Breast Cancer |
| SK-BR-3 | Breast Cancer |

Results of Anticancer Activity Testing

The diglucosyldiethylenetriamine compound (1) was active against breast cancer cell lines, MDA-MB-435. Compound (1) inhibited growth of the MDA-MB-435 cells by 50% ($GI_{50}$) at 1.72 $\mu$M concentration. Total growth inhibition (TGI) was observed at 3.23 $\mu$M concentration. The lethal concentration to kill 50% of the cells ($LC_{50}$) was at about 6 $\mu$M.

Compound (1) also displayed excellent antitumor activity against ovarian and renal cancer cell lines. The $GI_{50}$ against OVCAR-4 ovarian carcinoma cell lines was 1.63 $\mu$M and the TGI was about 3.5 $\mu$M and $LC_{50}$ was about 7.7 $\mu$M. When tested against renal cancer cell lines, CAKI-1, compound (1) had a $GI_{50}$ of 3.1 $\mu$M, and a TGI of about 10 $\mu$M and an $LC_{50}$ of 30 $\mu$M. Further, compound (1) showed moderate activity against colon cancer, KM12 cell lines. The $GI_{50}$ was about 10 $\mu$M, TGI was about 22 $\mu$M, and $LC_{50}$ was about 48 $\mu$M.

Although the forgoing invention has been described in some detail by way of illustration and example for purposes of clarity and understanding, it will be apparent to those skilled in the art that certain changes and modifications may be practical. Therefore, the description and examples should not be construed as limiting the scope of the invention, which is delineated by the appended claims.

Example 8
Crystallographic Studies

The crystal structure of the oligosaccharide of the invention diglucosyl diethylenetriamine (SPG-20) was studied with regard to its ability to bind the estrogen receptor (ER). Previous work on the estrogen receptor structure has determined that the overall shape of the binding site is similar to that of a boot and that estrogen has a 3-OH group, attached to a planar ring, which fits into the "toe" region of the boot. Other known ER ligands, such as tamoxifen and raloxifene, have a similar structure. It has previously been shown that the 3-OH/4-OH hydrogen bonds to a glutamic acid residue in the estrogen receptor itself, and that is thought to stabilize the binding. The rest of the pocket is not crucial, and as large ligands such as tamoxifen and raloxifene bind, has been shown to undergo conformational changes.

As shown in FIG. 1, the x-ray crystal structures pf SPG-20 were compared to the crystal structures of the other classes of known ER ligands. This comparison demonstrated that the overall dimensions of these molecules are similar. The arrows in FIG. 1 denote the portion of each of the known ER ligands that fits into the 3-OH region of the ER-ligand-binding site. Fitting (often a planar ring) into this "toe" region of the receptor has been shown to be essential for ER binding. Although SPG-20 is a non-classical ER ligand, other non-classical ligands (cyclic trimer) have been shown to bind and activate the receptor.

FIG. 2 shows the solvent accessible surface surrounding SPG-20 (left), in comparison with tamoxifen (right), whose geometries have been optimized using ab initio quantum methods. A coupled Schrodinger-Poisson-Boltzmann iterative procedure enabled the inclusion of solvation effects by using the ab initio electronic charge distribution to obtain the single and double layers of charge at the solvent accessible surface of the molecule. The polarization charge induced on these surface elements is mapped onto the nodes ("dots") from which the surface is comprised, and displayed simply as dark grey, light grey and black for negative, zero and positive values, respectively. The results shown in FIG. 2 provide a preliminary comparison of the polarization-induced charge on the saccharide (left) and tamoxifen (right). The results indicate similar induced electrostatic charges in the vicinity of the molecules that fit into the 3-OH "toe" binding site region (as denoted by the arrow). It should be noted that, although only the saccharide and tamoxifen are shown, all of the ER ligands have a similar charge distribution in that region.

Figure 3:
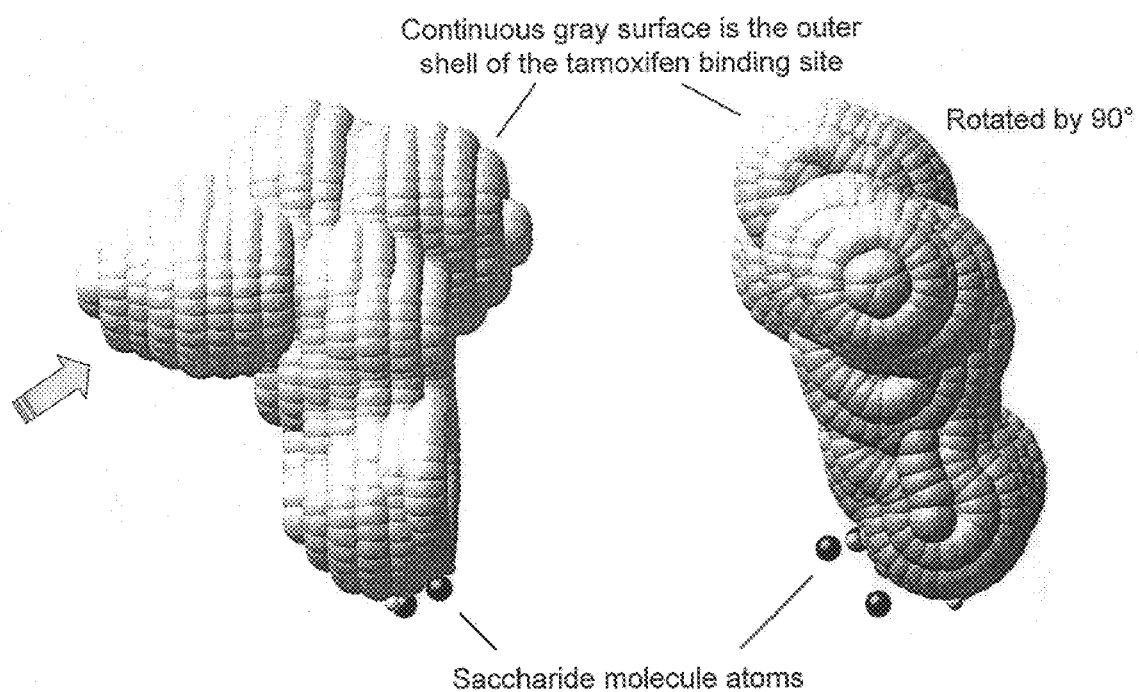
FIG. 3 is a schematic diagram of diglucosyl diethylenetriamine (SPG-20) placed into the crystallographically determined ER binding sites which are the result of complexing the ER with the specific ligands (e.g., estrogen, tamoxifen and raloxifene).

FIG. 3 shows the results of placing the saccharide molecule into the crystallographically determined ER binding sites which are the result of complexing the ER with the specific ligand (e.g., estrogen, tamoxifen and raloxifene). The minimum energy configuration of the molecule is determined by varying both the positions of its center of mass and its three-dimensional angular orientation within the binding sites. Atoms comprising the binding site itself were not allowed to relax. Interatomic potentials required for this minimization were determined by pairwise summation using local density methods and reflect the electronic overlap repulsion between the atoms comprising the molecule and those in the appropriate receptor binding site.

In FIG. 3, the shell of the binding site is depicted as a continuous gray surface, and is oriented with the 3-OH binding region on the left (left) and then rotated by 90° (right). A small part of one of the glucose units in the saccharide molecule can be seen sticking out the bottom. Thus, from these results, the saccharide molecule fits well into the tamoxifen-derived binding site.

We claim:

1. A method for inhibiting growth of cancer cells comprising contacting cancer cells with a compound of the formula:

wherein: each of $R_1$ and $R_2$ is independently a monosaccharide residue or an oligosaccharide residue; Z is an aliphatic polyamino linker that is the residue of an aliphatic polyamine comprising at least two amino groups, where there is at least one primary or secondary amino group per saccharide residue to be conjugated; and each of $R_1$ and $R_2$ is linked through its anomeric carbon at its 1 position to a different amino group of the aliphatic polyamino linker to form a glycosidic bond; provided that when each of $R_1$ and $R_2$ is the same and is a glucose, galactose, mannose, or cellobiose residue, Z is the residue of an aliphatic polyamine other than ethylenediamine or diaminopropane; and pharmaceutically acceptable salts and prodrugs thereof, such that growth of the cancer cells is inhibited.

2. The method of claim 1, wherein the cancer cells are breast cancer cells.

3. The method of claim 1, wherein the cancer cells are of a cancer selected from the group consisting of: leukemia, non-small-cell lung cancer, small-cell lung cancer, colon cancer, a cancer of the central nervous system, melanoma, ovarian cancer, renal cancer and prostate cancer.

4. The method according to claim 1, wherein Z is substituted with at least one substituent selected from the group consisting of halogen, lower alkyl, alkoxy, acyloxy, hydroxy, acetamido, amino, acyl, nitro, mercapto, benzyloxy, benzyl and phenyl.

5. The method according to claim 4, wherein each of $R_1$ and $R_2$ is an oligosaccharide residue.

6. The method according to claim 4, wherein at least one of $R_1$ and $R_2$ has a group other than hydrogen in equatorial conformation at the C2 position that is adjacent to the anomeric carbon atom linked to the aliphatic polyamine.

7. The method according to claim 6, wherein the group in equatorial conformation at the C2 position is a hydroxy, alkoxy, halo, lower alkyl, amino, N-acetyl, N-alkyl, N-hydroxy, N-alkoxy, aminothiol, amino alcohol, spermine, or nitro group.

8. The method according to claim 4, wherein each of the $R_1$ and $R_2$ is independently substituted by one or more of the groups: a lower alkyl, lower alkoxy, acyl, carboxy, carboxyamino, amino, acetamido, halo, thio, keto, phosphatyl or nitro; provided that the anomeric carbon has a free hydroxyl group to form a glycosidic linkage with the aliphatic polyamino linker.

9. The method according to claim 4, wherein $R_1$ is a monosaccharide residue and $R_2$ is an oligosaccharide residue.

10. The method according to claim 4, wherein each of $R_1$ and $R_2$ is a monosaccharide residue.

11. The method according to claim 4, wherein each of $R_1$ and $R_2$ is a hexose residue.

12. The method according to claim 11, wherein at least one of $R_1$ and $R_2$ has a group other than hydrogen in equatorial conformation at the C2 position that is adjacent to the anomeric carbon atom linked to the aliphatic polyamine.

13. The method according to claim 12, wherein the group in equatorial conformation at the C2 position is a hydroxy, alkoxy, halo, lower alkyl, amino, N-acetyl, N-alkyl, N-hydroxy, N-alkoxy, aminothiol, amino alcohol, spermine, or nitro group.

14. The method according to claim 11, wherein each of the hexose residues is independently substituted by one or more of the groups: a lower alkyl, lower alkoxy, acyl, carboxy, carboxyamino, amino, acetamido, halo, thio, keto, phosphatyl or nitro; provided that the anomeric carbon has a free hydroxyl group to form a glycosidic linkage with the aliphatic polyamino linker.

15. The method according to claim 4, wherein the aliphatic polyamino linker is the residue of diethylenetriamine.

16. The method according to claim 4, wherein each of $R_1$ and $R_2$ is the same and is a glucose, galactose, allose or fucose residue and the aliphatic polyamine linker is the residue of diethylenetriamine.

17. The method according to claim 4, wherein the prodrug further comprises a salt or lower hydrocarbon which can be hydrolyzed or solvated under physiological conditions.

18. The method according to claim 17, wherein the salt is sodium, potassium, or hemisulfate.

19. The method according to claim 17, wherein the hydrocarbon is methyl, ethyl or propyl.

20. The method according to claim 1, wherein each of the $R_1$ and $R_2$ is independently substituted by one or more of the groups: a lower alkyl, lower alkoxy, acyl, carboxy, carboxyamino, amino, acetamido, halo, thio, keto, phosphatyl or nitro; provided that the anomeric carbon has a free hydroxyl group to form a glycosidic linkage with the aliphatic polyamino linker.

21. The method according to claim 1, wherein each of $R_1$ and $R_2$ is an oligosaccharide residue.

22. The method according to claim 21, wherein at least one of $R_1$ and $R_2$ has a group other than hydrogen in equatorial conformation at the C2 position that is adjacent to the anomeric carbon atom linked to the aliphatic polyamine.

23. The method according to claim 22, wherein the group in equatorial conformation at the C2 position is a hydroxy, alkoxy, halo, lower alkyl, amino, N-acetyl, N-alkyl, N-hydroxy, N-alkoxy, aminothiol, amino alcohol, spermine, or nitro group.

24. The method according to claim 1, wherein $R_1$ is a monosaccharide residue and $R_2$ is an oligosaccharide residue.

25. The method according to claim 24, wherein at least one of $R_1$ and $R_2$ has a group other than hydrogen in equatorial conformation at the C2 position that is adjacent to the anomeric carbon atom linked to the aliphatic polyamine.

26. The method according to claim 25, wherein the group in equatorial conformation at the C2 position is a hydroxy, alkoxy, halo, lower alkyl, amino, N-acetyl, N-alkyl, N-hydroxy, N-alkoxy, aminothiol, amino alcohol, spermine, or nitro group.

27. The method according to claim 1, wherein each of $R_1$ and $R_2$ is a monosaccharide residue.

28. The method according to claim 27, wherein at least one of $R_1$ and $R_2$ has a group other than hydrogen in equatorial conformation at the C2 position that is adjacent to the anomeric carbon atom linked to the aliphatic polyamine.

29. The method according to claim 28, wherein the group in equatorial conformation at the C2 position is a hydroxy, alkoxy, halo, lower alkyl, amino, N-acetyl, N-alkyl, N-hydroxy, N-alkoxy, aminothiol, amino alcohol spermine, or nitro group.

30. The method according to claim 1, wherein each of $R_1$ and $R_2$ is a hexose residue.

31. The method according to claim 30, wherein at least one of $R_1$ and $R_2$ has a group other than hydrogen in equatorial conformation at the C2 position that is adjacent to the anomeric carbon atom linked to the aliphatic polyamine.

32. The method according to claim 31, wherein the group in equatorial conformation at the C2 position is a hydroxy, alkoxy, halo, lower alkyl, amino, N-acetyl, N-alkyl, N-hydroxy, N-alkoxy, aminothiol, amino alcohol, spermine, or nitro group.

33. The method according to claim 30, wherein each of the hexose residues is independently substituted by one or more of the groups: a lower alkyl, lower alkoxy, acyl, carboxy, carboxyamino, amino, acetamido, halo, thio, keto, phosphatyl or nitro; provided that the anomeric carbon has a free hydroxyl group to form a glycosidic linkage with the aliphatic polyamino linker.

34. The method according to claim 1, wherein the aliphatic polyamino linker is the residue of diethylenetriamine.

35. The method according to claim 1, wherein each of $R_1$ and $R_2$ is the same and is a glucose, galactose, allose or fucose residue and the aliphatic polyamine linker is the residue of diethylenetriamine.

36. The method according to claim 1, wherein the prodrug further comprises a salt or lower hydrocarbon which can be hydrolyzed or solvated under physiological conditions.

37. The method according to claim 36, wherein the salt is sodium, potassium, or hemisulfate.

38. The method according to claim 36, wherein the hydrocarbon is methyl, ethyl or propyl.

39. The method according to claim 1, wherein the compound has the following structure:

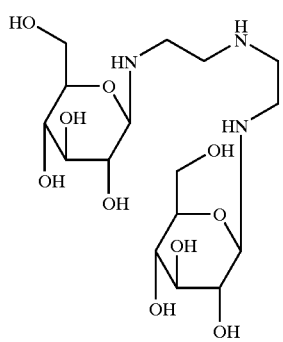

and pharmaceutically acceptable salts and prodrugs thereof.

40. A method for modulating estrogen receptor activity comprising contacting an estrogen receptor with a compound of the formula:

$$R_1-Z-R_2$$

wherein: each of $R_1$ and $R_2$ is independently a monosaccharide residue or an oligosaccharide residue; Z is an aliphatic polyamino linker that is the residue of an aliphatic polyamine comprising at least two amino groups, where there is at least one primary or secondary amino group per saccharide residue to be conjugated; and each of $R_1$ and $R_2$ is linked through its anomeric carbon at its 1 position to a different amino group of the aliphatic polyamino linker to form a glycosidic bond; provided that when each of $R_1$ and $R_2$ is the same and is a glucose, galactose, mannose, or cellobiose residue, Z is the residue of an aliphatic polyamine other than ethylenediamine or diaminopropane; and pharmaceutically acceptable salts and prodrugs thereof, such that estrogen receptor activity is modulated.

41. A method for treating, preventing or delaying onset of breast cancer in a subject having or at risk for breast cancer, the method comprising administering to the subject an effective amount of a compound of the formula:

$$R_1-Z-R_2$$

wherein: each of $R_1$ and $R_2$ is independently a monosaccharide residue or an oligosaccharide residue; Z is an aliphatic polyamino linker that is the residue of an aliphatic polyamine comprising at least two amino groups, where there is at least one primary or secondary amino group per saccharide residue to be conjugated; and each of $R_1$ and $R_2$ is linked through its anomeric carbon at its 1 position to a different amino group of the aliphatic polyamino linker to form a glycosidic bond; provided that when each of $R_1$ and $R_2$ is the same and is a glucose, galactose, mannose, or cellobiose residue, Z is the residue of an aliphatic polyamine other than ethylenediamine or diaminopropane; and pharmaceutically acceptable salts and prodrugs thereof.

42. A method for treating, preventing or delaying onset of osteoporosis in a subject having or at risk for osteoporosis, the method comprising administering to the subject an effective amount of a compound of the formula:

wherein: each of $R_1$ and $R_2$ is independently a monosaccharide residue or an oligosaccharide residue; Z is an aliphatic polyamino linker that is the residue of an aliphatic polyamine comprising at least two amino groups, where there is at least one primary or secondary amino group per saccharide residue to be conjugated; and each of $R_1$ and $R_2$ is linked through its anomeric carbon at its 1 position to a different amino group of the aliphatic polyamino linker to form a glycosidic bond; provided that when each of $R_1$ and $R_2$ is the same and is a glucose, galactose, mannose, or cellobiose residue, Z is the residue of an aliphatic polyamine other than ethylenediamine or diaminopropane; and pharmaceutically acceptable salts and prodrugs thereof.

43. A method for reducing risk of cardiovascular disease in a subject, the method comprising administering to the subject an effective amount of a compound of the formula:

wherein: each of $R_1$ and $R_2$ is independently a monosaccharide residue or an oligosaccharide residue; Z is an aliphatic polyamino linker that is the residue of an aliphatic polyamine comprising at least two amino groups, where there is at least one primary or secondary amino group per saccharide residue to be conjugated; and each of $R_1$ and $R_2$ is linked through its anomeric carbon at its 1 position to a different amino group of the aliphatic polyamino linker to form a glycosidic bond; provided that when each of $R_1$ and $R_2$ is the same and is a glucose, galactose, mannose, or cellobiose residue, Z is the residue of an aliphatic polyamine other than ethylenediamine or diaminopropane; and pharmaceutically acceptable salts and prodrugs thereof.

44. The method according to any one of claims 1 or 41–43, wherein at least one of $R_1$ and $R_2$ is a deoxy saccharide.

* * * * *